(12) United States Patent
Xie et al.

(10) Patent No.: US 11,993,598 B2
(45) Date of Patent: May 28, 2024

(54) COMPOUNDS FOR INHIBITING EGFR KINASE, PREPARATION METHODS AND USES THEREOF

(71) Applicant: WIGEN BIOMEDICINE TECHNOLOGY (SHANGHAI) CO., LTD., Shanghai (CN)

(72) Inventors: Yuli Xie, Shanghai (CN); Gang Cao, Shanghai (CN); Houxing Fan, Shanghai (CN)

(73) Assignee: WIGEN BIOMEDICINE TECHNOLOGY (SHANGHAI) CO., LTD., Shanghai (CN)

( * ) Notice: Subject to any disclaimer, the term of this patent is extended or adjusted under 35 U.S.C. 154(b) by 722 days.

(21) Appl. No.: 17/200,856

(22) Filed: Mar. 14, 2021

(65) Prior Publication Data
US 2021/0230161 A1 Jul. 29, 2021

Related U.S. Application Data

(63) Continuation of application No. PCT/CN2020/099916, filed on Jul. 2, 2020.

(30) Foreign Application Priority Data

Jul. 4, 2019 (CN) .......................... 201910600229.1

(51) Int. Cl.
| | | |
|---|---|---|
| C07D 471/06 | (2006.01) |
| A61K 31/454 | (2006.01) |
| A61K 31/4545 | (2006.01) |
| A61K 31/496 | (2006.01) |
| A61K 31/5377 | (2006.01) |
| A61P 35/00 | (2006.01) |
| C07D 401/04 | (2006.01) |
| C07D 401/14 | (2006.01) |
| C07D 403/14 | (2006.01) |
| C07D 407/14 | (2006.01) |
| C07D 417/14 | (2006.01) |
| C07D 491/08 | (2006.01) |
| C07D 491/10 | (2006.01) |
| C07D 491/107 | (2006.01) |
| C07D 498/08 | (2006.01) |
| C07D 519/00 | (2006.01) |

(52) U.S. Cl.
CPC ......... C07D 471/06 (2013.01); C07D 519/00 (2013.01)

(58) Field of Classification Search
CPC .. C07D 403/14; C07D 407/14; C07D 491/10; C07D 401/04; C07D 401/14; C07D 417/14; C07D 491/08; C07D 491/107; C07D 498/08; A61P 35/00; A61K 31/454; A61K 31/4545; A61K 31/496; A61K 31/5377

See application file for complete search history.

(56) References Cited

U.S. PATENT DOCUMENTS

2018/0208581 A1* 7/2018 Zhu .................. C07D 403/04

FOREIGN PATENT DOCUMENTS

| CN | 109328059 A | 2/2019 |
|---|---|---|
| EP | 3323817 A1 | 5/2018 |
| EP | 3492462 A1 | 6/2019 |
| WO | 2017008761 A1 | 1/2017 |
| WO | 2017120429 A1 | 7/2017 |
| WO | 2018019204 A1 | 2/2018 |

* cited by examiner

*Primary Examiner* — John M Mauro
(74) *Attorney, Agent, or Firm* — SZDC Law PC

(57) ABSTRACT

The present invention provides a compound of formula (I) or a pharmaceutically acceptable salt thereof, a preparation method and application thereof. The compounds can selectively inhibit the activity of epidermal growth factor receptor (EGFR) mutants, and shows good inhibitory effect towards mutant EGFR and anti-proliferative activity against cancer cells. Thus they can be used for treating tumors and related diseases.

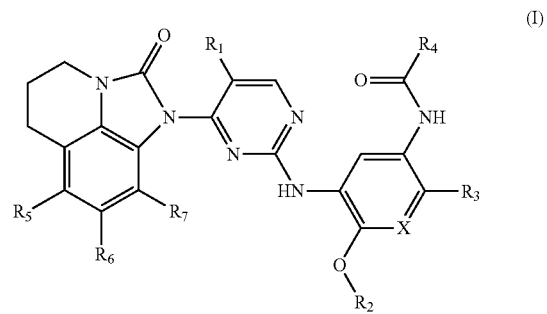

3 Claims, 1 Drawing Sheet

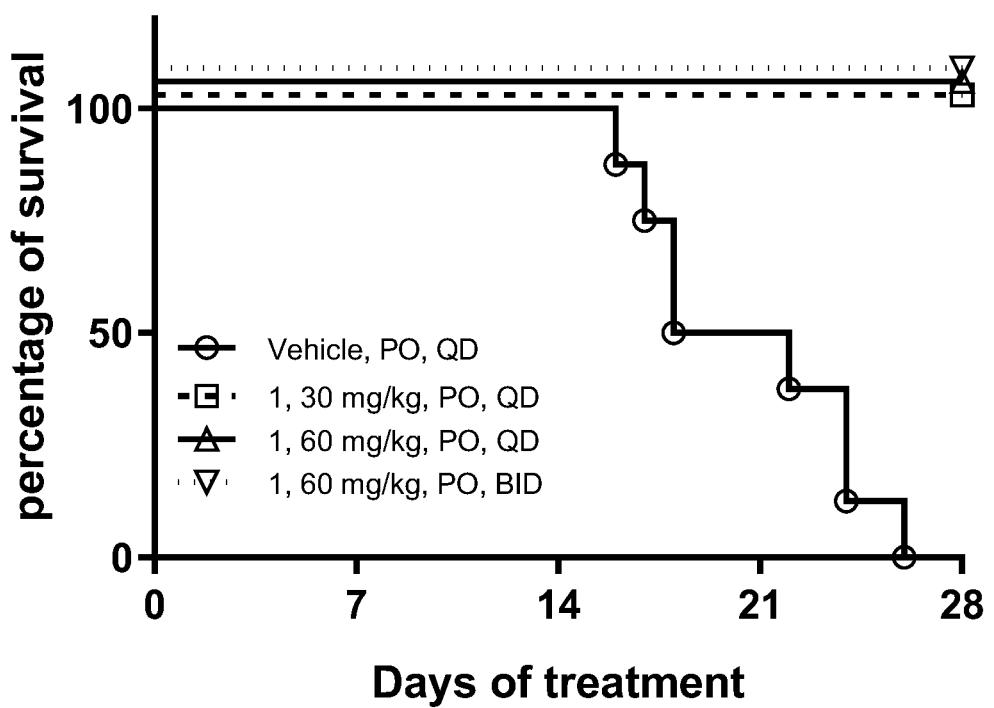

COMPOUNDS FOR INHIBITING EGFR KINASE, PREPARATION METHODS AND USES THEREOF

This application is a Continuation Application of PCT/CN2020/099916, filed on Jul. 2, 2020, which claims the benefits of Chinese Patent Application No. 201910600229.1, filed on Jul. 4, 2019, which is incorporated herein by reference in its entirety.

FIELD OF THE INVENTION

The invention relates to the fields of pharmaceuticals, and more specifically, relates to a series of EGFR inhibitors, the preparation methods and the uses thereof.

BACKGROUND OF THE INVENTION

The epidermal growth factor receptor (EGFR) is a receptor tyrosine kinase of the ErbB family at the plasma membrane. Other members of the ErbB family include ERBB2 (HER2), ERBB3 (HER3) and ERBB4 (HER4). EGFR promotes cell growth through the activation of MAPK and PI3K signaling transduction pathway. Overactivated EGFR via mutation, amplification or ovexpression has been identified in multiple solid tumors especially lung cancer.

The prevalence of EGFR mutation in non-small cell lung cancer (NSCLC) is 50% in east Asia and 15% in Europe and America. Most EGFR mutations occur in exon 18 through exon 21. The first generation EGFR tyrosine inhibitors (TKIs) including Gefitinib and Erlotinib mainly target mutations at exon 18, 19 and 21. Resistance, however, inevitably develops during the course of the treatment. EGFR-T790M mutation accounts for over 60% of the acquired resistance to the first generation TKIs. Afatinib, a second generation irreversible EGFR inhibitor, is active against T790M, however, is associated with substantial toxicity including rash and diarrhea due to its activity towards wild type EGFR. The third generation of EGFR TKI, AZD9291, specifically tackles T790M, and is approved as treatments for patients with EGFR T790M mutation positive non-small cell lung cancer.

In addition to the aforementioned classical EGFR mutations, exon 20 insertions constitute the third largest group of EGFR mutations with a frequency of 4-10% among all EGFR mutations, more common in women, non-smokers, asian population, and adenocarcinoma patients, and are associated with similar clinical characteristics to those of classical mutations.

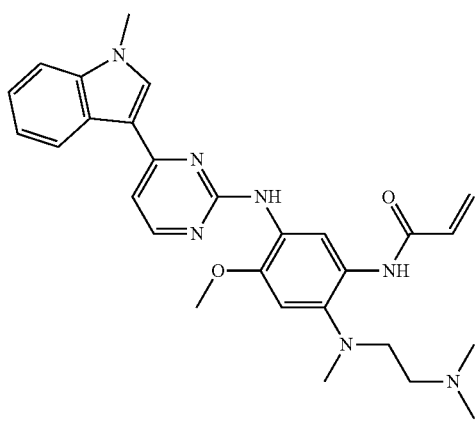

AZD9291

Mutations in exon 20 clustered between amino acid 762 and 823 and all of them are insertions except T790M. In addition to EGFR, around 2% of NSCLC patients carry her2 mutations, 90% of which are exon 20 insertions. Exon 20 insertion mutations in Her2 occur in a structurally analogous position as those in EGFR with similar molecular features and drug sensitivity. Together, they are broadly categorized as exon 20 insertions. 122 subtypes of EGFR exon 20 insertions were identified so far, with Asp770_Asn771ins being the most prevalent followed by Val769_Asp770ins, Ala767_Val769ins and Ser768_Asp770ins. Whereas, the most common variant for exon20 mutation in Her2 is A775_G776insYVM, representing 70% of the cases. Exon 20 insertions in EGR and Her2 all promote ligand-independent activation.

A majority of EGFR exon 20 insertions are naïve and some of them are acquired. Aside from lung cancer, exon 20 insertions are also observed in a rare form of head and neck cancer known as sinonasal squamous cell carcinoma. In view of the presence of exon 20 insertions in a significant number of patients, agents that can inhibit EGFR harboring the exon 20 insertions may be especially useful for this group of patients. Many studies show, however, exon 20 insertions, particularly those after amino acid 764 are not sensitive to the approved TKIs, and there are limited therapeutic options available. Poziotinib and Mobocertinib, two TKIs against exon 20 insertions, are now under clinical investigation. Among them, Poziotinib is associated with severe adverse effects possibly due to concomitant inhibition of wild-type EGFR. Therefore, development of TKIs with selectivity to exon 20 insertions over wild-type EGFR is warranted. a new generation of TKIs disclosed in this patent demonstrate superior biochemical and cellular activity towards T790M and exon 20 insertion mutations over wild type EGFR.

SUMMARY OF THE INVENTION

The present invention provides a compound of general formula (I) a pharmaceutically acceptable salt thereof:

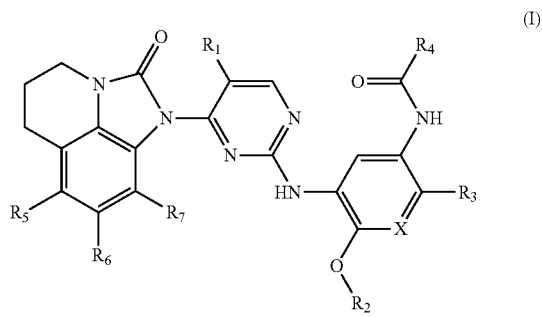

(I)

Wherein:
X is selected from the group consisting of N and CH;
$R_1$ is selected from the group consisting of hydrogen, halogen, C1-6 alkyl, C3-6 cycloalkyl, —C(O)OR$_8$ and CN;
$R_2$ is selected from the group consisting of C1-6 alkyl, deuterated C1-6 alkyl, C3-6 cycloalkyl and C1-6 haloalkyl;
$R_3$ is selected from the group consisting of —NR$_9$(CH$_2$)$_2$NR$_9$'R$_9$",

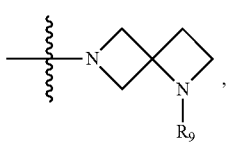

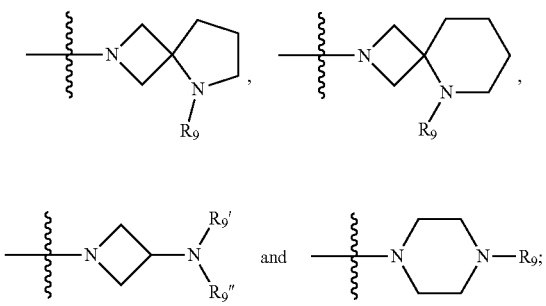

$R_4$ is

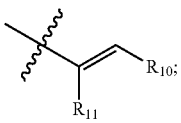

$R_5$, $R_6$, and $R_7$ are independently selected from the group consisting of hydrogen, halogen, C1-6 alkyl, C1-6 haloalkyl, C1-6 alkoxy and CN;

$R_8$ is selected from the group consisting of hydrogen, C1-6 alkyl and C1-6 haloalkyl; $R_9$ is selected from the group consisting of hydrogen, C1-6 alkyl, deuterated C1-6 alkyl and C1-6 haloalkyl;

$R_9'$ and $R_9''$ are independently selected from the group consisting of hydrogen. C1-6 alkyl, C3-6 cycloalkyl, deuterated C1-6 alkyl and C1-6 haloalkyl, or $R_9'$ and $R_9''$ together with the nitrogen connected thereto form a heterocycle, the heterocycle is unsubstituted or optionally substituted with 1-3 groups selected from the group consisting of halogen, C1-6 alkyl, C1-3 alkoxy, methylthio, methanesulfonyl and C1-6 haloalkyl;

$R_{10}$ is selected from the group consisting of hydrogen, halogen, C1-6 alkyl and —$CH_2NR_{12}'R_{12}''$;

$R_{11}$ is selected from the group consisting of hydrogen, halogen and C1-6 alkyl; and $R_{12}$ and $R_{12}'$ are independently selected from the group consisting of hydrogen, C1-6 alkyl and C1-6 haloalkyl, or $R_{12}'$ and $R_{12}''$ together with the nitrogen connected thereto form a heterocycle, the heterocycle is unsubstituted or optionally substituted with 1-3 groups selected from the group consisting of halogen, C1-6 alkyl and C1-6 haloalkyl.

In the general formula (I), $R_1$ is preferably selected from the group consisting of hydrogen, halogen, C1-6 alkyl, —C(O)OR$_8$ or CN; and $R_5$, $R_6$ and $R_7$ are preferably independently selected from the group consisting of hydrogen and halogen.

The present invention provides compounds of formula (I) capable of inhibiting one or more EGFR-activated or drug-resistant mutants, e. g., a T790M drug-resistant mutant, an exon 20 insertion-activated mutant, and thus such compounds can be used in cancer therapy regimens for patients who have gotten drug resistance to existing therapies based on EGFR inhibitors.

The present invention provides compounds of that general formula (I) have more potent inhibition of EGFR formed by activated or resistant mutant than wild-type EGFR due to the reduced toxicity associated with wild-type EGFR inhibition, so that such compounds are more suitable for use as therapeutic agents, particularly for the treatment of cancer.

The invention provides a preparation method of a compound of the general formula (I) The present invention provides a pharmaceutical composition comprising a compound of formula (I) or a pharmaceutically acceptable salt thereof, and a pharmaceutically acceptable carrier, excipient or diluent.

The present invention provides the use of a compound of formula (I) or a pharmaceutically acceptable salt thereof in the treatment of diseases mediated by EGFR-activated or drug-resistant mutants in mammals, particularly humans, and particularly in cancer treatment.

The present invention provides a method of treating disease, particularly cancer, mediated by EGFR-activated or drug-resistant mutants in mammal, particularly humans, comprising administering to a patient a compound of formula (I) or a pharmaceutically acceptable salt thereof, or a pharmaceutical composition comprising a therapeutically effective amount of a compound of formula (I) and a pharmaceutically acceptable carrier, excipient or diluent.

The present invention provides a method for selectively inhibiting EGFR-activated or drug-resistant mutants compared to wild-type EGFR, comprising contacting or administering to a patient a biological sample of a compound of formula (I) or a pharmaceutically acceptable salt thereof or a pharmaceutical composition thereof.

The cancer referred to in the present invention may be selected from hepatocellular carcinoma, lung cancer, pancreatic cancer, breast cancer, cervical cancer, endometrial cancer, colorectal cancer, gastric cancer, lung cancer, nasopharyngeal cancer, ovarian cancer, prostate cancer, leukemia, lymphoma, non-hodgkin lymphoma myeloma, glioma, glioblastoma, melanoma, gastrointestinal stromal tumor (GIST), thyroid cancer, cholangiocarcinoma, renal cancer, anaplastic large cell lymphoma, acute myeloid leukemia (AML), multiple myeloma or mesothelioma.

In the present invention, particularly preferred compounds of formula (I) or pharmaceutically acceptable salts thereof include the following:

TABLE 1
| No | Structure |
|---|---|
| 1 | 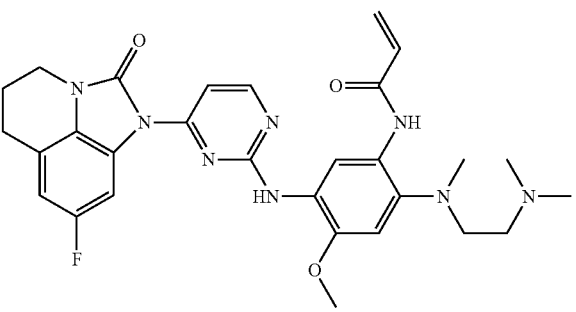 [SMILES: C=CC(=O)Nc1cc(Nc2nccc(-n3c(=O)n4c5c(cc(F)cc53)CCC4)n2)c(OC)cc1N(C)CCN(C)C] |
| 2 | 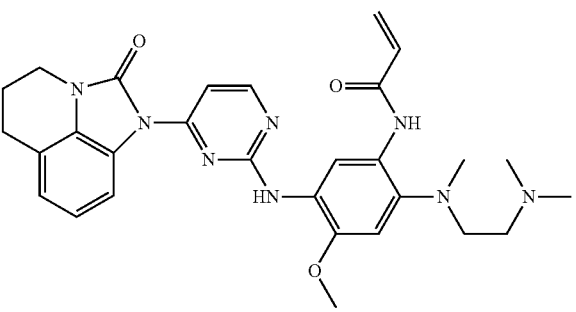 |
| 3 | 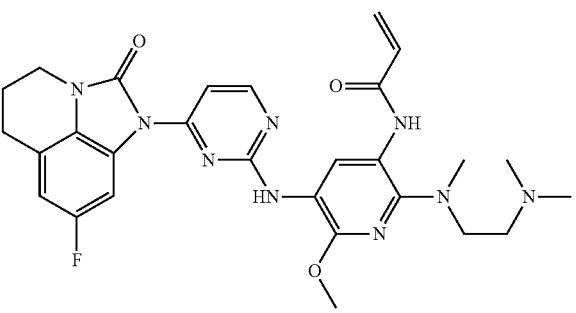 [SMILES: C=CC(=O)Nc1cc(Nc2nccc(-n3c(=O)n4c5c(cc(F)cc53)CCC4)n2)c(OC)nc1N(C)CCN(C)C] |
| 4 | 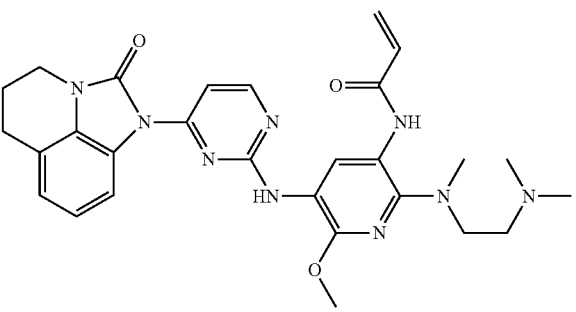 [SMILES: C=CC(=O)Nc1cc(Nc2nccc(-n3c(=O)n4c5c(cccc53)CCC4)n2)c(OC)nc1N(C)CCN(C)C] |
| 5 | 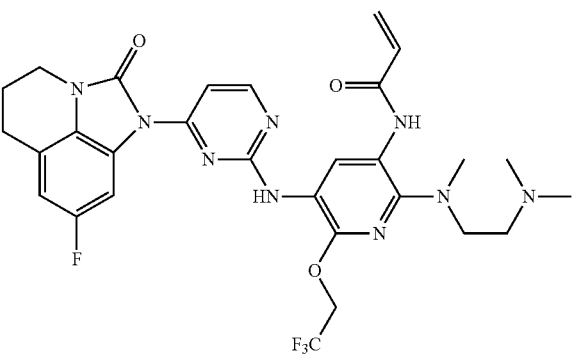 |

TABLE 1-continued
| No | Structure |
|---|---|
| 6 | 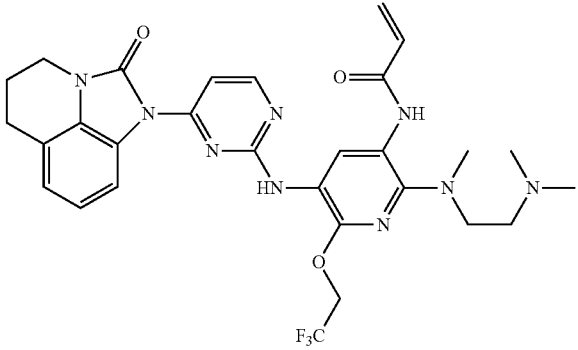 [SMILES: C=CC(=O)Nc1cc(Nc2nccc(-n3c(=O)n4c5c(cccc53)CCC4)n2)c(OCC(F)(F)F)nc1N(C)CCN(C)C] |
| 7 | 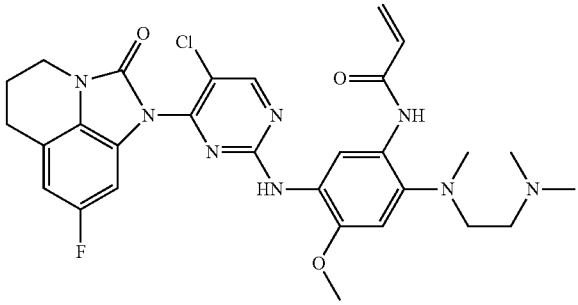 [SMILES: C=CC(=O)Nc1cc(Nc2ncc(Cl)c(-n3c(=O)n4c5c(cc(F)cc53)CCC4)n2)c(OC)cc1N(C)CCN(C)C] |
| 8 | 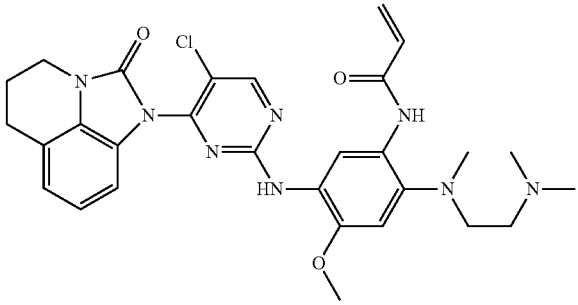 [SMILES: C=CC(=O)Nc1cc(Nc2ncc(Cl)c(-n3c(=O)n4c5c(cccc53)CCC4)n2)c(OC)cc1N(C)CCN(C)C] |
| 9 | 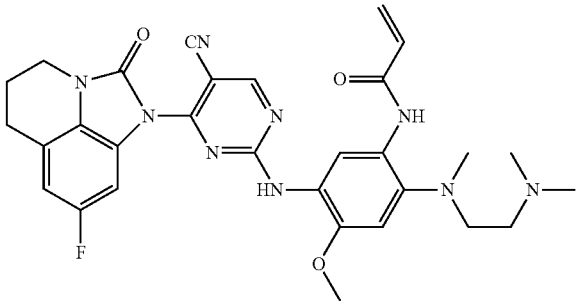 [SMILES: C=CC(=O)Nc1cc(Nc2ncc(C#N)c(-n3c(=O)n4c5c(cc(F)cc53)CCC4)n2)c(OC)cc1N(C)CCN(C)C] |

TABLE 1-continued
| No | Structure |
|---|---|
| 10 | 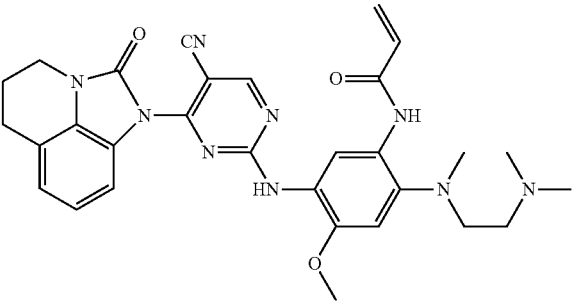 |
| 11 | 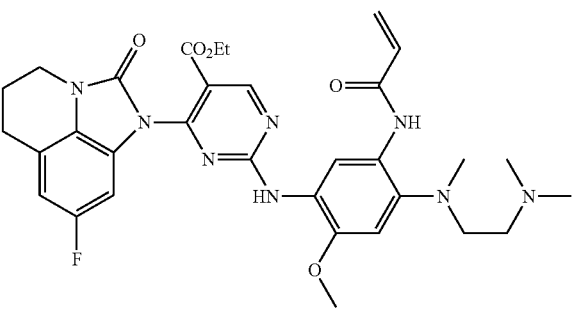 [SMILES: C=CC(=O)Nc1cc(Nc2ncc(C(=O)OCC)c(-n3c(=O)n4c5c(cc(F)cc53)CCC4)n2)c(OC)cc1N(C)CCN(C)C] |
| 12 | 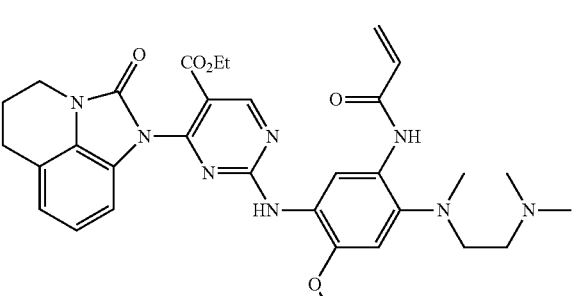 |
| 13 | 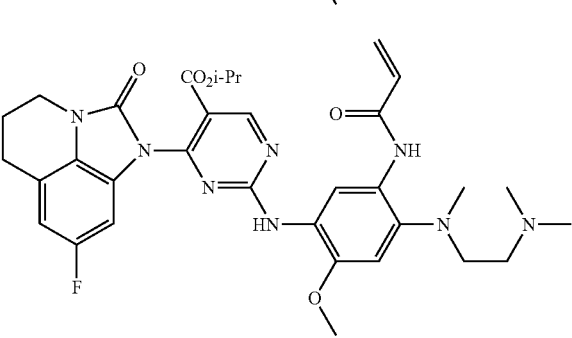 |
| 14 | 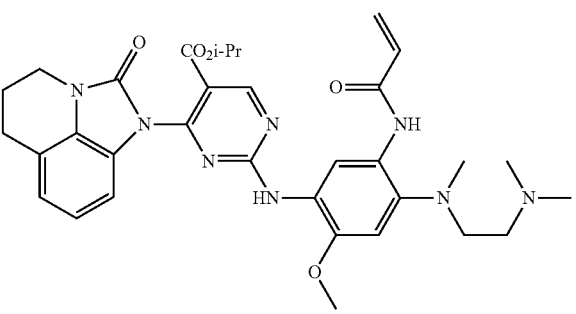 |

TABLE 1-continued

| No | Structure |
|---|---|
| 15 | 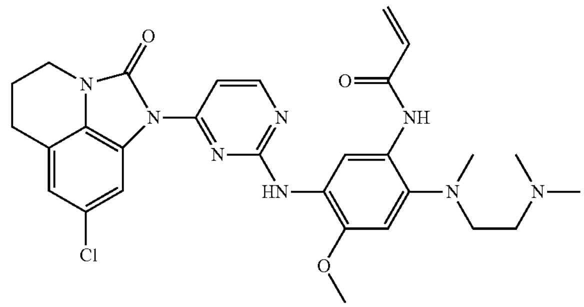 |
| 16 | 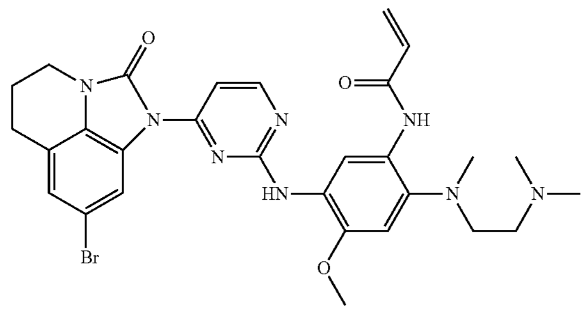 |
| 17 | 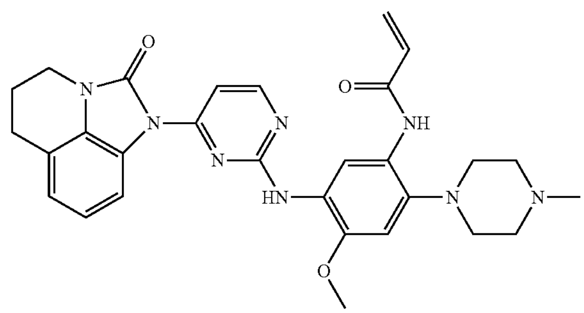 [SMILES: C=CC(=O)Nc1cc(Nc2nccc(-n3c(=O)n4c5c(cccc53)CCC4)n2)c(OC)cc1N1CCN(C)CC1] |
| 18 | 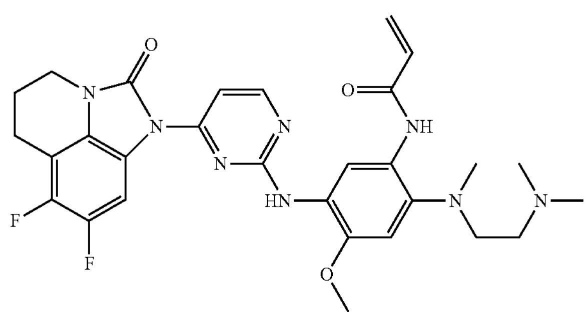 [SMILES: C=CC(=O)Nc1cc(Nc2nccc(-n3c(=O)n4c5c(c(F)c(F)cc53)CCC4)n2)c(OC)cc1N(C)CCN(C)C] |
| 19 | 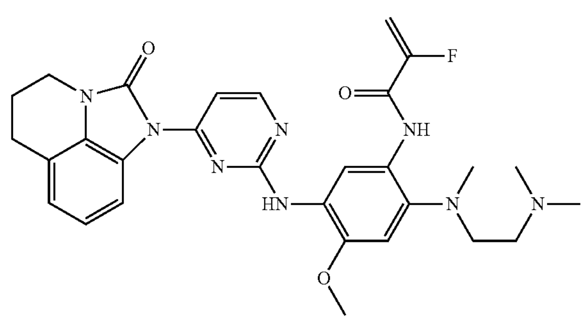 [SMILES: C=C(F)C(=O)Nc1cc(Nc2nccc(-n3c(=O)n4c5c(cccc53)CCC4)n2)c(OC)cc1N(C)CCN(C)C] |

TABLE 1-continued
| No | Structure |
|---|---|
| 20 | 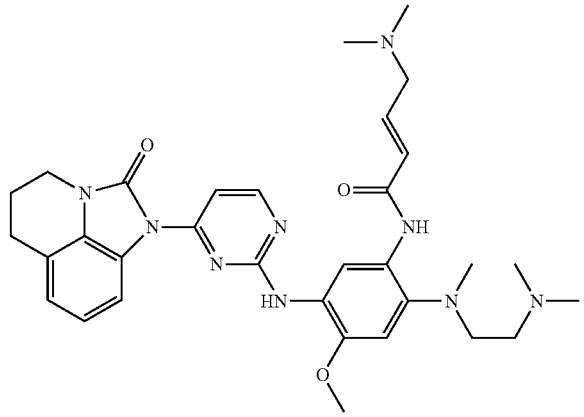 [SMILES: COc1cc(N(C)CCN(C)C)c(NC(=O)/C=C/CN(C)C)cc1Nc1nccc(-n2c(=O)n3c4c(cccc42)CCC3)n1] |
| 21 | 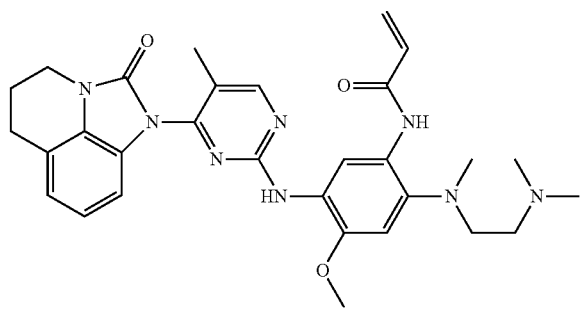 [SMILES: C=CC(=O)Nc1cc(Nc2ncc(C)c(-n3c(=O)n4c5c(cccc53)CCC4)n2)c(OC)cc1N(C)CCN(C)C] |
| 22 | 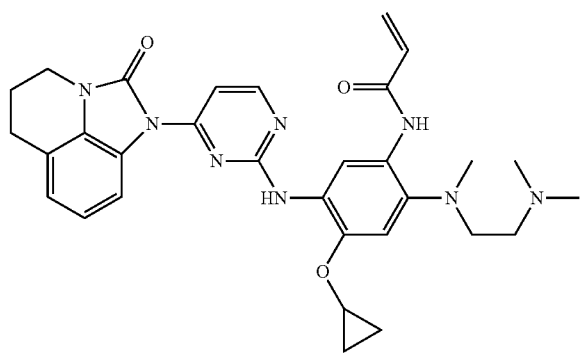 [SMILES: C=CC(=O)Nc1cc(Nc2nccc(-n3c(=O)n4c5c(cccc53)CCC4)n2)c(OC2CC2)cc1N(C)CCN(C)C] |
| 23 | 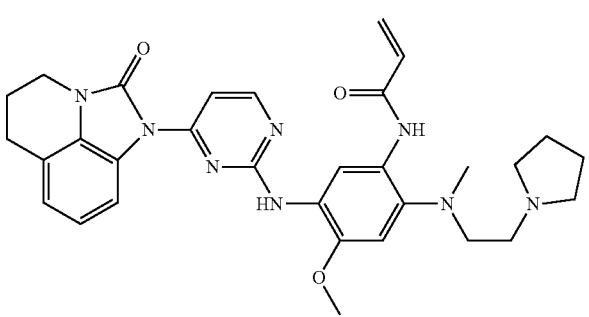 [SMILES: C=CC(=O)Nc1cc(Nc2nccc(-n3c(=O)n4c5c(cccc53)CCC4)n2)c(OC)cc1N(C)CCN1CCCC1] |

TABLE 1-continued
| No | Structure |
|---|---|
| 24 | 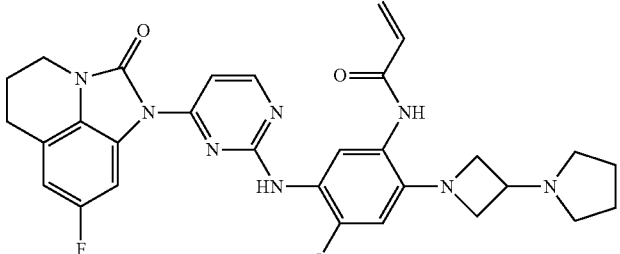 |
| 25 | 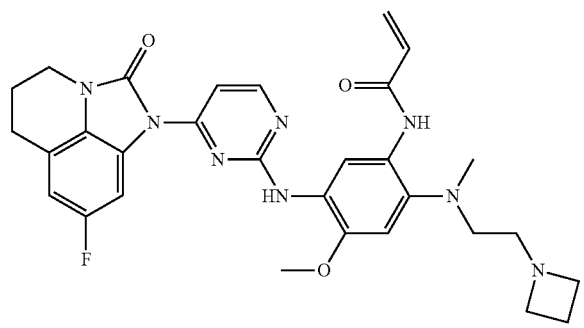 [SMILES: C=CC(=O)Nc1cc(Nc2nccc(-n3c(=O)n4c5c(cc(F)cc53)CCC4)n2)c(OC)cc1N(C)CCN1CCC1] |
| 26 | 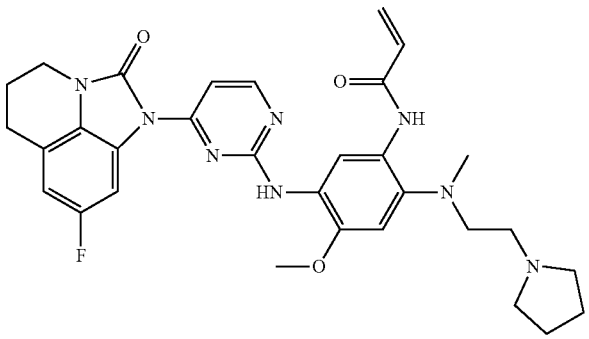 [SMILES: C=CC(=O)Nc1cc(Nc2nccc(-n3c(=O)n4c5c(cc(F)cc53)CCC4)n2)c(OC)cc1N(C)CCN1CCCC1] |
| 27 | 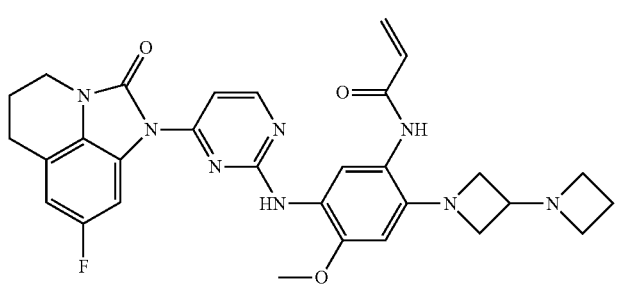 [SMILES: C=CC(=O)Nc1cc(Nc2nccc(-n3c(=O)n4c5c(cc(F)cc53)CCC4)n2)c(OC)cc1N1CC(N2CCC2)C1] |
| 28 | 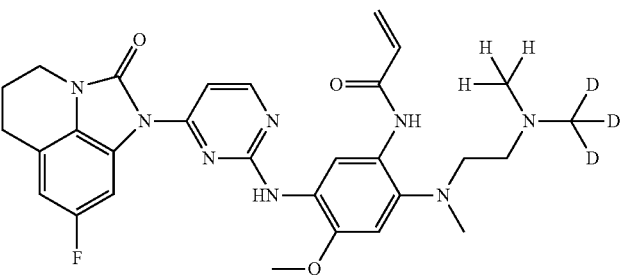 |

TABLE 1-continued

| No | Structure |
|----|-----------|
| 29 | 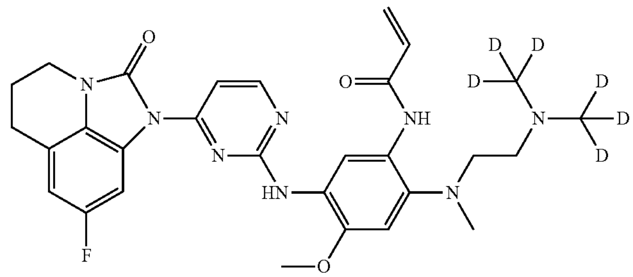 [SMILES: [2H]C([2H])([2H])N(CCN(C)c1cc(OC)c(Nc2nccc(-n3c(=O)n4c5c(cc(F)cc53)CCC4)n2)cc1NC(=O)C=C)C([2H])([2H])[2H]] |
| 30 | 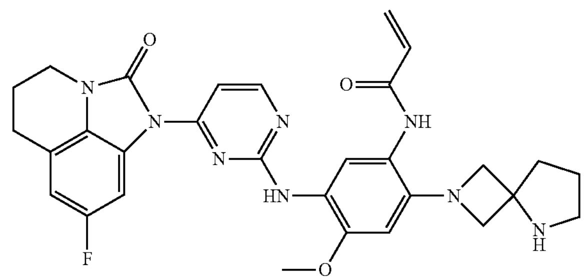 [SMILES: C=CC(=O)Nc1cc(Nc2nccc(-n3c(=O)n4c5c(cc(F)cc53)CCC4)n2)c(OC)cc1N1CC2(CCCN2)C1] |
| 31 | 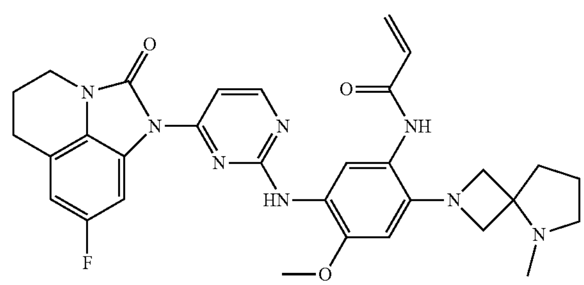 |
| 32 | 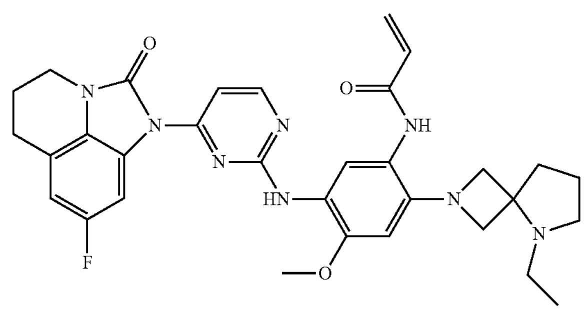 [SMILES: C=CC(=O)Nc1cc(Nc2nccc(-n3c(=O)n4c5c(cc(F)cc53)CCC4)n2)c(OC)cc1N1CC2(CCCN2CC)C1] |
| 33 | 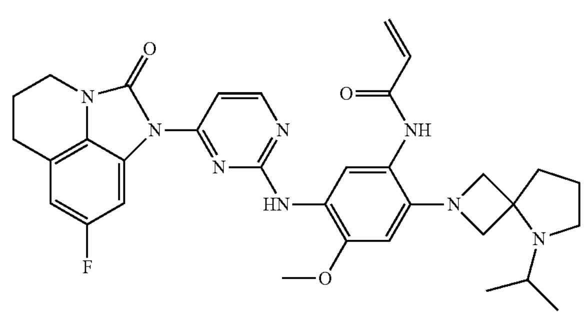 [SMILES: C=CC(=O)Nc1cc(Nc2nccc(-n3c(=O)n4c5c(cc(F)cc53)CCC4)n2)c(OC)cc1N1CC2(CCCN2C(C)C)C1] |

TABLE 1-continued
| No | Structure |
|---|---|
| 34 | 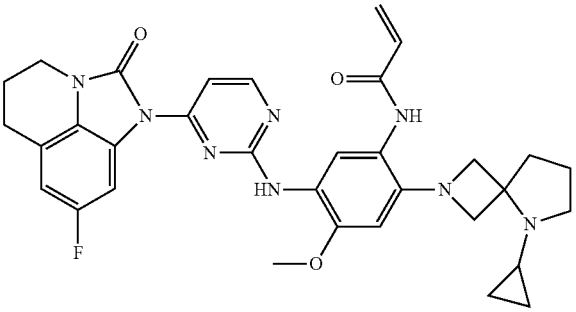 [SMILES: C=CC(=O)Nc1cc(Nc2nccc(-n3c(=O)n4c5c(cc(F)cc53)CCC4)n2)c(OC)cc1N1CC2(CCCN2C2CC2)C1] |
| 35 | 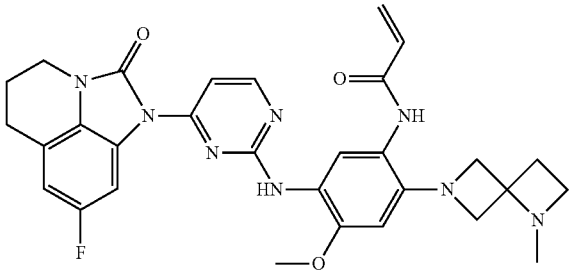 [SMILES: C=CC(=O)Nc1cc(Nc2nccc(-n3c(=O)n4c5c(cc(F)cc53)CCC4)n2)c(OC)cc1N1CC2(CCN2C)C1] |
| 36 | 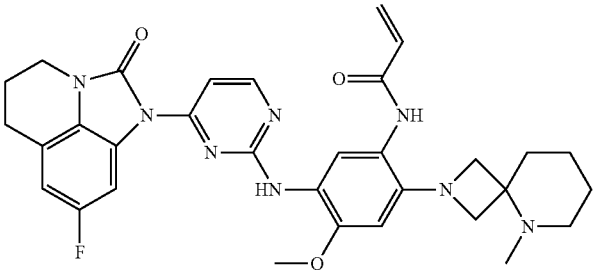 [SMILES: C=CC(=O)Nc1cc(Nc2nccc(-n3c(=O)n4c5c(cc(F)cc53)CCC4)n2)c(OC)cc1N1CC2(CCCCN2C)C1] |
| 37 | 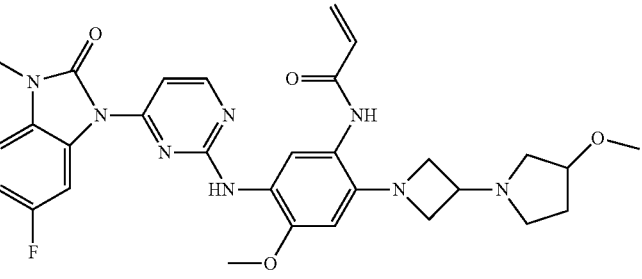 |
| 38 | 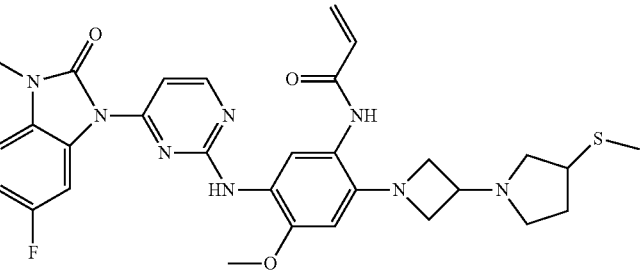 |

TABLE 1-continued

| No | Structure |
|---|---|
| 39 | 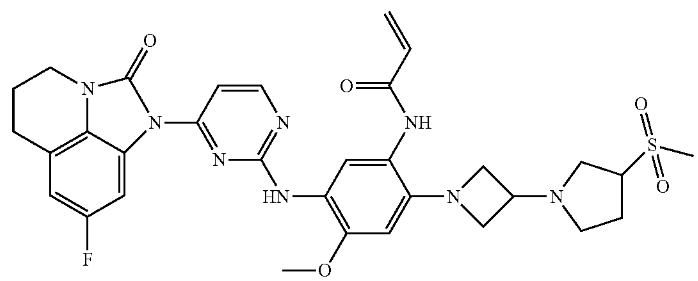 [SMILES: C=CC(=O)Nc1cc(Nc2nccc(-n3c(=O)n4c5c(cc(F)cc53)CCC4)n2)c(OC)cc1N1CC(N2CCC(S(C)(=O)=O)C2)C1] |
| 40 | 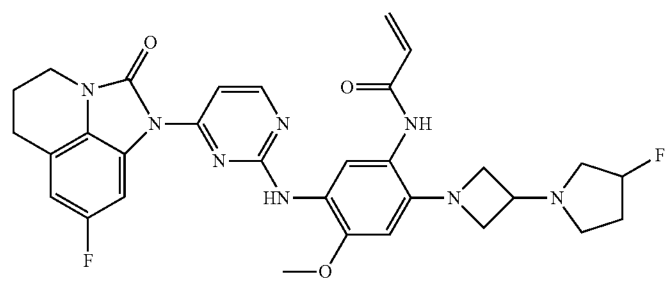 [SMILES: C=CC(=O)Nc1cc(Nc2nccc(-n3c(=O)n4c5c(cc(F)cc53)CCC4)n2)c(OC)cc1N1CC(N2CCC(F)C2)C1] |
| 41 | 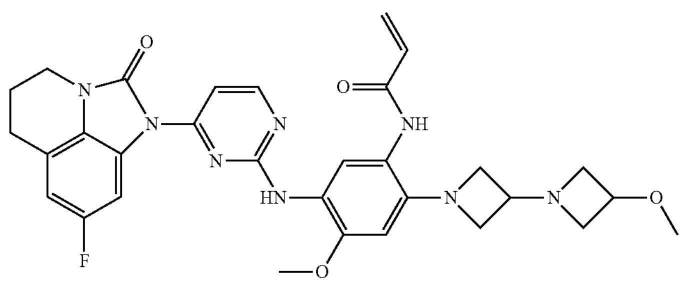 [SMILES: C=CC(=O)Nc1cc(Nc2nccc(-n3c(=O)n4c5c(cc(F)cc53)CCC4)n2)c(OC)cc1N1CC(N2CC(OC)C2)C1] |
| 42 | 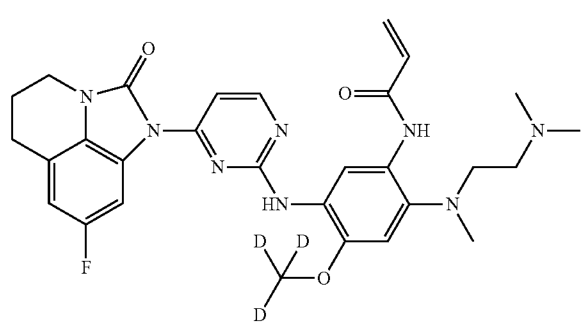 [SMILES: [2H]C([2H])([2H])Oc1cc(N(C)CCN(C)C)c(NC(=O)C=C)cc1Nc1nccc(-n2c(=O)n3c4c(cc(F)cc42)CCC3)n1] |
| 43 | 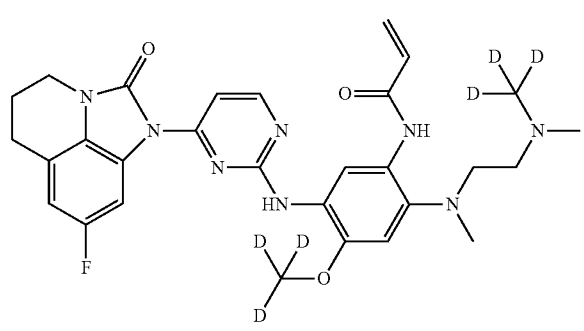 [SMILES: [2H]C([2H])([2H])Oc1cc(N(C)CCN(C)C([2H])([2H])[2H])c(NC(=O)C=C)cc1Nc1nccc(-n2c(=O)n3c4c(cc(F)cc42)CCC3)n1] |

TABLE 1-continued
| No | Structure |
|---|---|
| 44 | 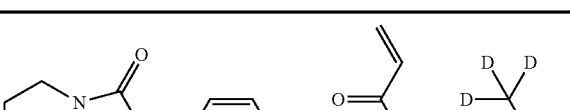 |
The present invention provides a process for preparing a compound of formula I comprising the following steps:
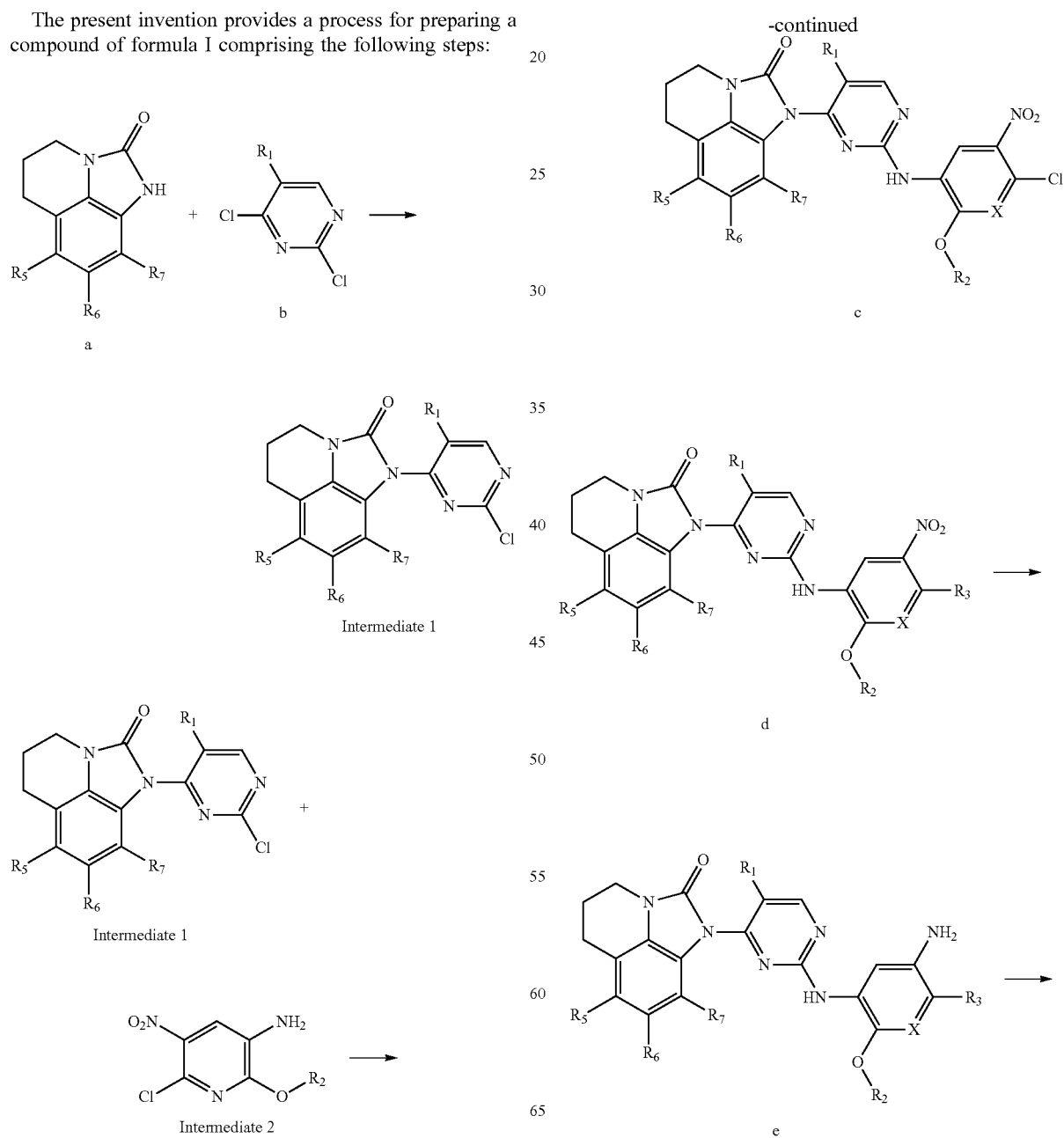

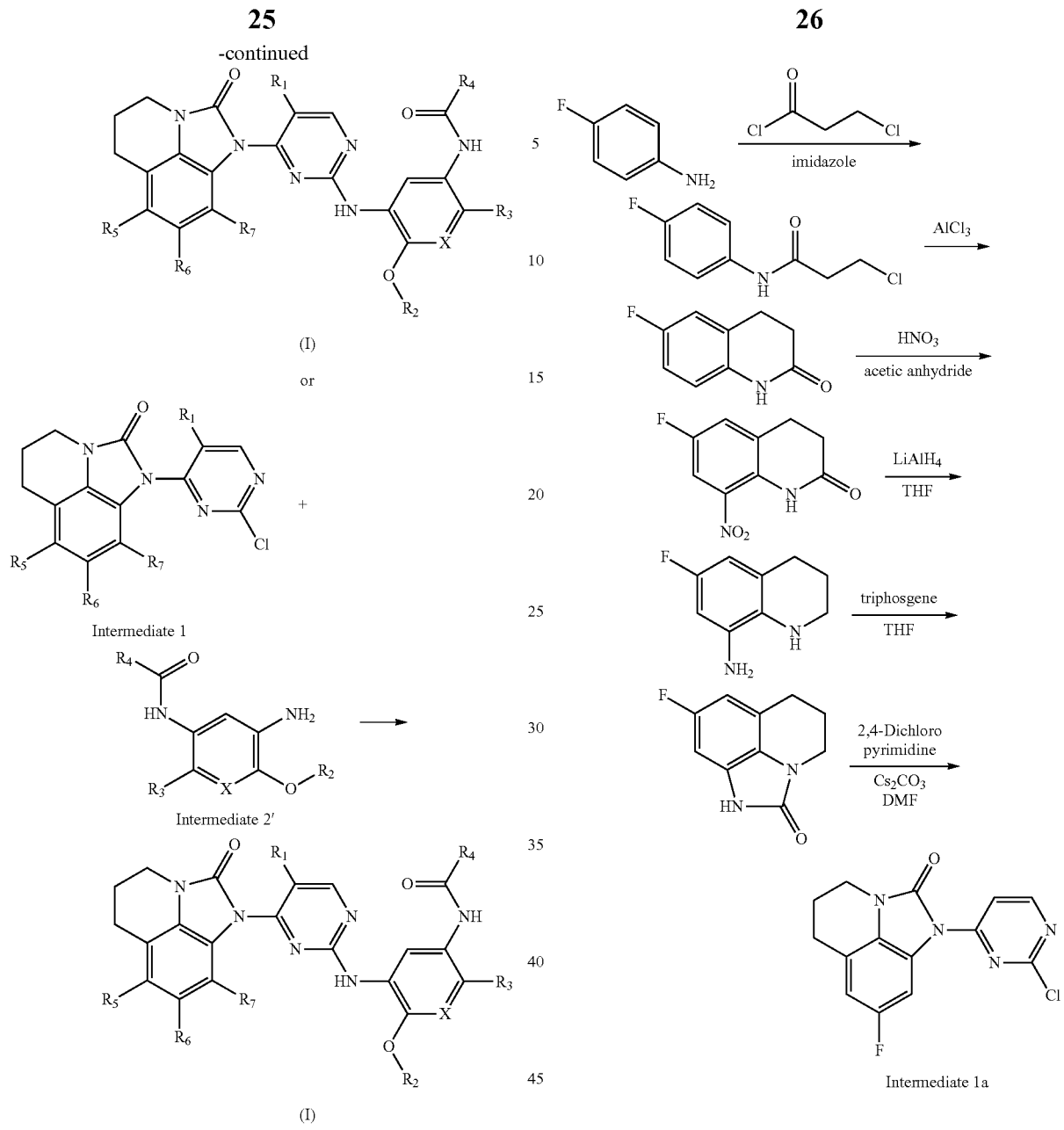

(I)

Wherein, $R_1$, $R_2$, $R_3$, $R_4$, $R_5$, $R_6$ and $R_7$ have the same definitions as defined in the above general formula (I).

Taking compounds (a) and (b) as starting materials, carrying out substitution reaction under basic condition to obtain intermediate 1, conducting substitution or couple reaction using intermediate 1 and the intermediate 2 to obtain compound (c), compound (c) is carried out nucleophilic substitution to obtain compound (d), reduction the nitro group of the compound (d) to obtain compound (e), compound (e) is further conducted to acylation to obtain a compound (I); Or intermediate 1 and intermediate 2' are directly conducted to substitution or coupling reaction to obtain compound (I).

In one embodiment, when intermediate 1 is intermediate 1a, the compound of formula (I) is prepared as following:

In one embodiment, when intermediate 1 is intermediate 1b, the compound of formula (I) is prepared as following:

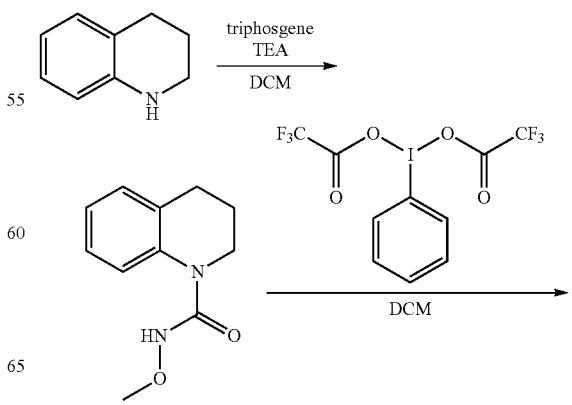

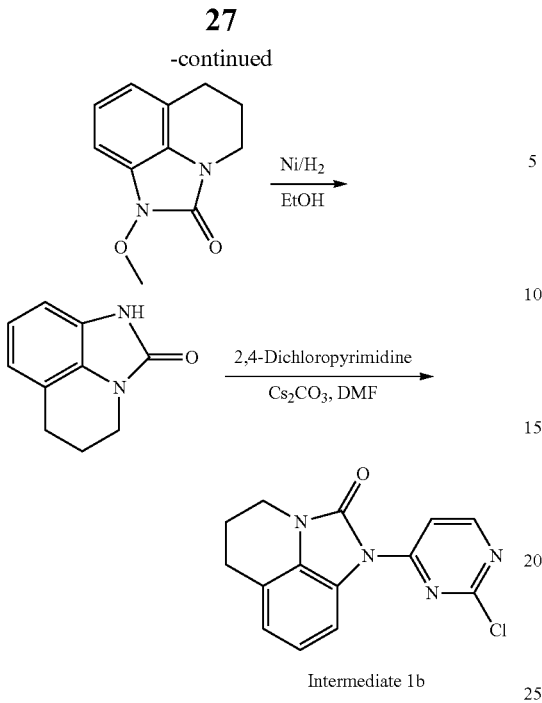

In one embodiment of that present invention for the preparation of a compound of formula (I), the process for the preparation of intermediate 2, intermediate 2' includes the following steps

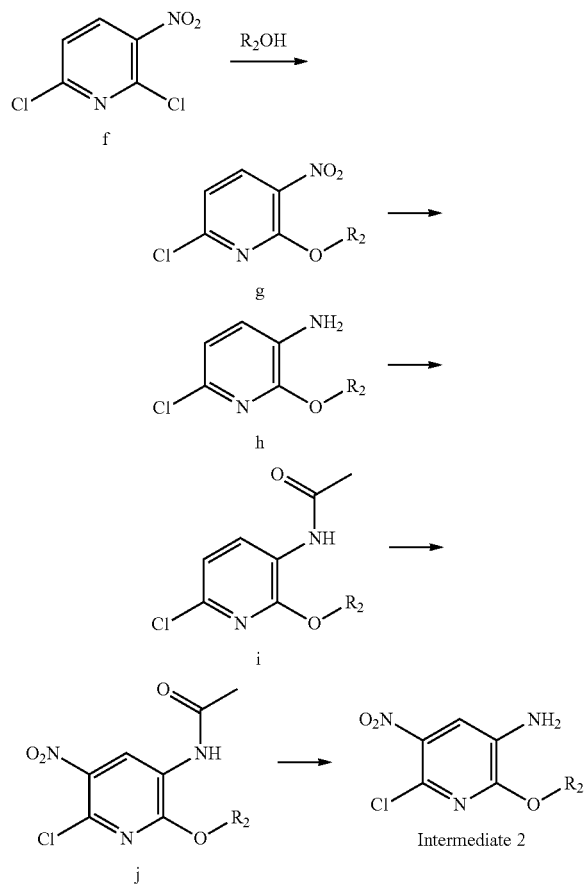

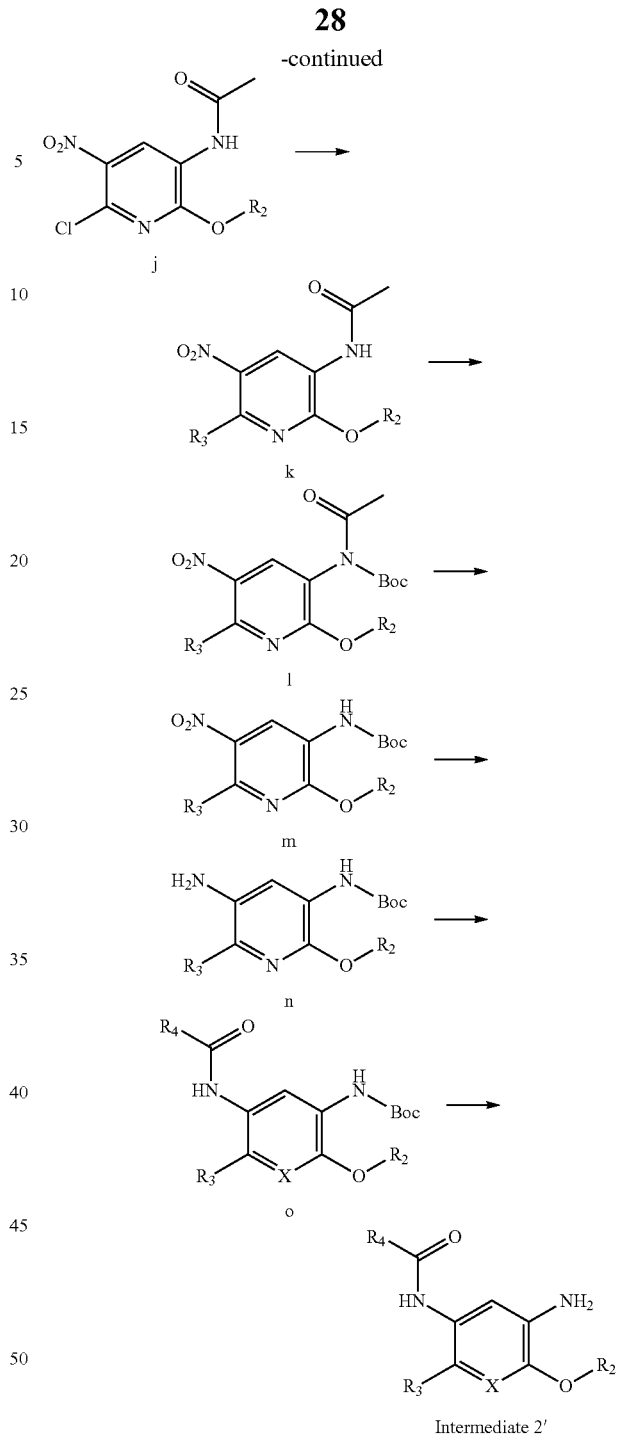

Wherein $R_2$, $R_3$ and $R_4$ have the same definitions as defined in the above general formula (I).

Taking 2,6-dichloro-3-nitropyridine as starting materials, carrying out etherification reaction to obtain compound (g), which is conducted to reduction nitro group of the compound (g) to obtain compound (h), the compound (h) is carried out acylation to obtain compound (i), then compound (i) is conducted to nitration reaction to obtain compound (j), which is further deprotected to obtain intermediate 2.

The compound (j) reacts with $R_3H$ by substitution to obtain compound (k), compound (k) is protected by Boc to obtain compound (l), which is carried out deacetylation protection to obtain compound (m), the nitro group of the compound (in) is reduced to obtain compound (n), compound (n) is further acylated to obtain compound (o), and finally compound (o) is conducted to deprotection to obtain intermediate 2'.

In the preparation method of the intermediates 2 and 2', the etherification reaction is carried out under the action of strong base, wherein the strong base is including but is not limited to sodium hydride, potassium hydride, sodium hydroxide, potassium hydroxide, sodium ethoxide and sodium methoxide; Methods of reduction the nitro group use the conventional reductants known in the art, including but not limited to iron powder, zinc powder, sodium sulfide, $H_2/PtO_2$; The upper protecting group or the deprotecting group is carried out by conventional methods well known in the art under suitable acidic or basic conditions.

"Halogen" (or "halo") refers to fluorine, chlorine, bromine or iodine.

"C1-6 alkyl" refers to a linear or branched alkyl group having 1 to 6 carbon atoms, preferably a linear or branched alkyl group having 1 to 4 carbon atoms. Branched chain means that one or more alkyl groups of 1 to 4 carbon atoms such as methyl, ethyl or propyl, etc. are attached to the linear alkyl group. Preferred C1-6 alkyl groups include, but are not limited to, methyl, ethyl, n-propyl, isopropyl, n-butyl, isobutyl, tert-butyl and the like.

"Deuterated alkyl" means that one or more hydrogen atoms in the alkyl group are replaced by deuterium. For example, three hydrogen atoms in the methyl group are all replaced by deuterium to form deuterated methyl group $CD_3$.

"C1-6 haloalkyl" refers to a C1-6 alkyl group as defined above containing one or more halogen atom substituents.

"C1-6 heteroalkyl" means that C1-6 alkyl as defined above containing one or more substituents selected from the group consisting of O, S, N, —(S=O)—, —(O=S=O)— and the like.

"C3-6 cycloalkyl" refers to a non-aromatic monocyclic or polycyclic group having 3 to 6 carbon atoms, preferably 3 to 6 carbon atoms. Preferred monocyclic C3-6 cycloalkyl groups include, but are not limited to, cyclopropyl, cyclopentyl, cyclohexyl and the like.

"C1-6 alkoxy" refers to a C1-6 alkyl-O— group bonding to the parent moiety by oxygen, wherein C1-6 alkyl is as described above. Preferred C1-6 alkoxy groups include, but are not limited to, methoxy, ethoxy, n-propoxy, isopropoxy and n-butoxy.

Any of the abovementioned functional groups of the present invention may be unsubstituted or substituted by substituents described herein. The term "substituted" (or substitute) refers to the replacement of one or more hydrogen atoms at a specified atom with a group selected from the specified group, provided that the normal valence state of the specified atom is not exceeded, and the substitution results in a stable compound. Combination of that substituents and/or variable are permitted only when the combination forms a stable compound.

The invention also includes pharmaceutically acceptable salt of a compound of formula (I). The term "pharmaceutically acceptable salt" refers to a relatively non-toxic acid addition salt or base addition salt of a compound of the present invention. The acid addition salt is a salt of that a compound of formula (I) according to the invention with suitable inorganic or organic acid, which salt can be prepared in the final separation and purification of the compound or can be prepared by reacting the purified compound of formula (I) in its free base form with suitable organic or inorganic acid. Representative acid addition salt includes hydrobromide, hydrochloride, sulfate, bisulfate, sulfite, acetate, oxalate, valerate, oleate, palmitate, stearate, laurate, borate, benzoate, lactate, phosphate, hydrogen phosphate, carbonate, bicarbonate, toluate, citrate, maleate, fumarate, succinate, tartrate, benzoate, methanesulfonate, p-toluenesulfonate, gluconate, lactate, laurate and that like. The base addition salt is a salt of that a compound of formula (I) of the present invention with suitable inorganic or organic base, including, for example, salt with alkali metal, alkaline earth metals, quaternary ammonium cation, such as sodium, lithium, potassium, calcium, magnesium, tetramethylammonium, tetraethylammonium and the like; Amine salt, including salt formed with ammonia ($NH_3$), primary ammonia, secondary ammonia or tertiary amine, such as methylamine salt, dimethylamine salt, trimethylamine salt, triethylamine salt, ethylamine salt and the like.

The enzyme activity assays showed that the compound of the invention has good activity against exon 20 insertion mutant; Cell assays, namely in vitro antiproliferation assays of activated mutant cells, i.e., exon 20 insertion-type activated mutant cells, drug-resistant tumor cells and wild-type EGFR human skin cells showed that the compound has good antiproliferative activity on activated mutant cells or drug-resistant mutant tumor cells, but weak antiproliferative activity on wild-type EGFR cancer cells with good selectivity. The compound of the invention is useful for the treatment of disease or conditions mediated by the activity of EGFR-activated or resistant mutants, in particular treatment of cancer. Such cancer includes, but are not limited to, such as hepatocellular carcinoma, lung cancer, head and neck cancer, pancreatic cancer, breast cancer, cervical cancer, endometrial cancer, colorectal cancer, gastric cancer, lung cancer, nasopharyngeal cancer, ovarian cancer, prostate cancer, leukemia, lymphoma, non-hodgkin's lymphoma myeloma, glioma, glioblastoma, melanoma, gastrointestinal stromal tumor (GIST), thyroid cancer, cholangiocarcinoma, renal cancer, anaplastic large cell lymphoma, acute myeloid leukemia (AML), multiple myeloma or mesothelioma, especially for epidermal growth factor receptor 790 threonine-to-methionine mutation (EGFR T790M) timor type and activated type mutation, exon 20 insertion type activated mutation tumor types have better application.

It is to be understood that both the foregoing general description and the following detailed description of the invention is exemplary and explanatory and is intended to provide a further explanation of the invention as claimed.

It is to be understood that various change or modifications may be made by those skilled in the art without departing from the scope and spirit of the invention, and it will be apparent to those skilled in the art that such equivalents may also fall within the scope of the invention as defined by the appended claims.

BRIEF DESCRIPTION OF DRAWINGS

FIG. 1 shows the effects of compound 1 on the survival rate of PC9 brain in-situ nude mice.

DETAILED DESCRIPTION OF THE INVENTION

Hereinafter, embodiments of the present invention will be described in detail.

EXAMPLES

The invention is further illustrated below with specific examples. It should be understood that these examples are only for illustrating the present invention and are not intended to limit the scope of the present invention, and the present invention is not limited to these examples. Those skilled in the art will readily understand that these compounds can be prepared using known variations of the conditions and processes of the following preparation methods. The starting materials used in the present invention without particular description are commercially available.

Abbreviations: room temperature (RT, rt); aqueous solution (aq.); petroleum ether (PE); ethyl acetate (EA); dichloromethane (DCM); methanol (MeOH); ethanol (EtOH); tetrahydrofuran (THF); dimethylformamide (DMF); dimethyl sulfoxide (DMSO); triethylamine (TEA); diisopropylethylamine (DI(P)EA); 4-dimethylaminopyridine (DMAP); palladium on carbon (Pd/C); equivalent (eq.); gram/milligram (g/mg); mole/millimole (mol/mmol); Litre/millitre (L/mL); min (s)); hours (h, hr, hrs); nitrogen ($N_2$); nuclear magnetic resonance (NMR); thin layer chromatography (TLC).

General Synthetic Method:

Unless otherwise specified, all reactions are conducted under inert gas (e.g., argon or nitrogen) using commercially available reagents and anhydrous solvents without further conduct.

The mass spectra were recorded using a liquid chromatography-mass spectrometer (LC-MS) (Agilent 6120B single-and four-stage LC-MS). Nuclear magnetic resonance spectra (such as hydrogen ($^1H$), carbon ($^{13}C$), phosphorus ($^{31}P$), and fluorine ($^{19}F$) were recorded using a BrukerAMX-400, Gemini-300, or AMX-600 NMR spectrometer in a deuterated solvent such as deuterated chloroform, deuterated methanol, deuterated water, or deuterated dimethylsulfoxide with the deuterated solvent peak as the reference standard. The chemical shift δ is in ppm, and the coupling constant (j) is in Hertz (Hz). The coupling splitting peaks in the NMR spectrum are expressed as wide single peak (brs), single peak (s), double peaks (d), double double double peaks (dd), triple peak (t), quadruple peak (q) and multiple peaks (m).

DETAILED DESCRIPTION OF THE INVENTION

1. Preparation Examples of the Intermediates of the Present Invention

Intermediate 1a: Synthesis of 1-(2-chloropyrimidin-4-yl)-8-fluoro-5,6-dihydro-4H-imidazo[4,5,1-ij]quinolin-2(1H)-one Intermedite 1a

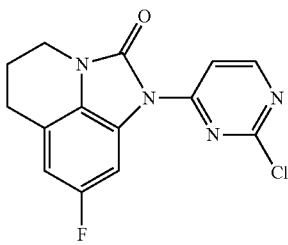

Step 1: Synthesis of 3-chloro-N-(4-fluorophenyl)propenamide

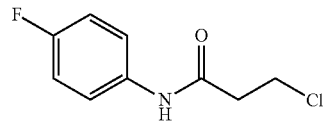 [SMILES: O=C(CCCl)Nc1ccc(F)cc1]

3-Chloropropionyl chloride (653 g, 1 eq) was dissolved in 6.5 L of dichloromethane, and the starting material 4-fluoroaniline (783.6 g, 1.05 eq) was added dropwise under a dry ice/ethanol bath while maintaining the internal temperature between 0 to 10° C., a large amount of solids were precipitated. After the dropwise addition, the mixture was further stirred for 0.5 h, and imidazole (405 g, 1.01 eq) was added in batches (with obvious temperature rise) to maintain the internal temperature between 0-10° C. The reaction was completed after stirring for 1 h, the reaction solution was poured into diluted hydrochloric acid, separated, the organic phase was concentrated until a large amount of solids were precipitated, 800 mL of PE/EA(5/1) was added, stirred overnight, filtered, and washed with PE/EA (5/1) to obtain 950 g of 3-chloro-N-(4-fluorophenyl)propenamide as a white solid. MS(ESI): m/z=202 [M+H]$^+$, $^1H$ NMR (400 MHz, DMSO-$d_6$) δ 10.16 (s, 1H), 7.71-7.60 (m, 2H), 7.23-7.13 (m, 2H), 3.91 (t, J=6.3 Hz, 2H), 2.84 (t, J=6.3 Hz, 2H).

Step 2: Synthesis of 6-fluoro-3,4-dihydroquinolin-2(1H)-one

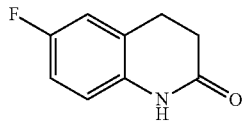

In a 5 L three-necked flask, 3-chloro-N-(4-fluorophenyl) propionamide (820 g, 1 eq) was added, followed by the addition of anhydrous aluminum trichloride (1640 g, 3 eq) under stirring, followed by nitrogen replacement for three times. The external temperature was set at 60° C., and the flask was stirred until molten state (the internal temperature was increased to 70° C.). After the internal temperature was decreased, the flask was heated to 100° C. (the internal temperature was 97° C.), and the mixture was stirred for 4 h. LCMS showed the reaction convention was about 58%, while 500 g of aluminum trichloride was added, and the mixture was further stirred for 4 h, LCMS showed the reaction convention was about 73%, and additional 200 g of aluminum trichloride was added and stirred for 4 h, LCMS showed only litter unconvented starting material. When the mixture was cooled to 40° C., DCM (2 L) was added into the mixture, then THF (6 L) was dropwise added into the mixture with intense exotherm. EA (3 L) was added and water was added continuously to separate out a large amount of precipitations. the organic phase was separated out, the organic phase was concentrated, and the aqueous phase was filtered. the combined products were respectively slurried with EA and water to obtain 600 g wet product as a white solid. MS(ESI): m/z=166 [M+H], $^1H$ NMR (400 MHz, DMSO-d$_6$) δ 10.16 (s, 1H), 7.71-7.61 (m, 2H), 7.23-7.13 (m, 2H), 3.92 (t, J=6.3 Hz, 2H), 2.85 (t, J=6.3 Hz, 2H).

Step 3: Synthesis of 6-fluoro-8-nitro-3,4-dihydroquinolin-2(1H)-one

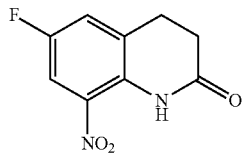

6-Fluoro-3,4-dihydroquinoline-2(1H)-one (700 g, 1 eq) was added into a 5 L three-neck flask, then 3.5 L of acetic anhydride was added, controlling the internal temperature to be 15-20° C., concentrated nitric acid (485 g, 1.2 eq) was slowly added dropwise, the solution became clear after the addition, further stirring at 25° C. for 30 min, then a large amount of solids were precipitated, pouring the reaction solution into water (20 L), stirring until the hydrolysis was completed, filtered, washed the filter cake with water until the washing solution became colorless, and dried to obtain 700 g of desired intermediate as a yellow solid; MS(ESI): m/z=211 [M+H]$^+$, HNMR: $^1$H NMR (400 MHz, DMSO-d$_6$) δ 9.84 (s, 1H), 7.91 (dd, J=8.9, 2.9 Hz, 1H), 7.70 (dd, J=8.2, 2.8 Hz, 1H), 3.15-3.04 (m, 2H), 2.63 (dd, J=8.3, 6.7 Hz, 2H).

Step 4: Synthesis of 6-fluoro-1,2,3,4-tetrahydroquinolin-8-amine

LiAlH$_4$ (48 g, 1.27 mol) was dissolved in THF (1 L) and a suspension of 6-fluoro-8-nitro-3,4-dihydroquinoline-2(1H)-one (89 g, 0.42 mol) in THF (100 mL) was added portionwise, maintaining the internal temperature between 5 to 10° C. After the dropwise addition was completed, the mixture was naturally restored to 12° C. and stirred for 0.5 h. Then the mixture was cooled to below 0° C., water (48 mL), 15% NaOH (48 mL) and water (144 mL) were successively quenched while maintaining the internal temperature below 5° C., and diatomaceous earth (90 g) was added. After stirring for 30 min below 5° C., the mixture was filtered with diatomaceous earth, washed with THF, the filter cake was slurried with THF again, filtered, and the organic phase was concentrated. The residual was purified by column chromatography (the mobile phase PE/EA ratio was 1/10, 1/4, and 2/3 contained 0.1% TEA) to obtain 57 g desired intermediate as wine-red oily liquid; MS (ESI): m/z=167 [M+H]$^+$.

Step 5: Synthesis of 8-fluoro-5,6-dihydro-4H-imidazo[4,5,1-ij]quinolin-2(1H)-one

6-Fluoro-8-amino-1,2,3,4-tetrahydroquinoline (166 g, 1 mol) was dissolved in THF (1 L) and a suspension of triphosgene (118 g, 0.4 mol) in THF (300 mL) was added dropwise while maintaining the internal temperature between 5 to 10° C. After the completion of addition, stirring was continued for 0.5 h, imidazole (160 g, 20 mol) was added dropwise, the internal temperature was maintained between 10-20° C., and the stirring was continued for 15 min after the temperature was restored to room temperature. Under the supervision of LCMS, after the starting materials was completed, 1 L of 13% NaCl solution was added, followed by addition of THF (1 L), separated the organic phase, extracted with THF (2 L*2), dried and concentrated, the residual was slurried with EA overnight, and filtrated to obtain 168 g of the desired intermediate as a light-brown solid MS(ESI): m/z=193 [M+H].

Step 6: Synthesis of 1-(2-chloropyrimidin-4-yl)-8-fluoro-5,6-dihydro-4H-imidazo-[4,5,1-ij]quinolin-2(1H)-one Intermedite 1a

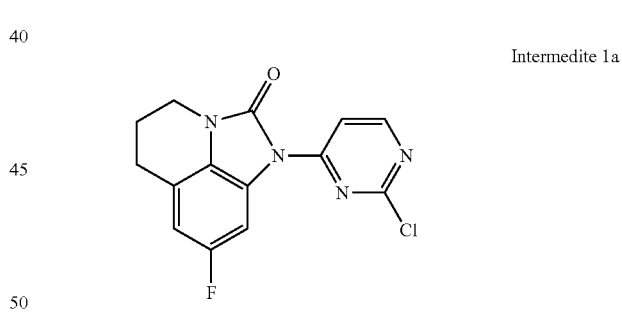

8-Fluoro-5,6-dihydro-4H-imidazole[4,5,1-ij]quinoline-2(1H)-one (36 g, 0.19 mol) and 2,4-dichloropyrimidine (34 g, 0.23 mol) were dissolved in DMF (400 mL), cesium carbonate (122 g, 0.37 mol) was added, and the mixture was stirred for 4 h at room temperature. The reaction was completed determined by LCMS. The mixture was diluted with water (250 mL), solid was filtered, and the crude sample was further purified by column chromatography (DCM/EA, 100/1), concentrated to about 50 mL, slurried with PE (200 mL) and filtered to obtain 45 g of desired intermediate as a white solid; MS (ESI): m/z=305 [M+H]$^+$, $^1$H NMR (400 MHz, DMSO-d$_6$) δ 8.81 (d, J=5.7 Hz, 1H), 8.42 (d, J=5.8 Hz, 1H), 7.75 (d, J=9.7 Hz, 1H), 7.00 (d, J=9.6 Hz, 1H), 3.82 (t, J=5.5 Hz, 2H), 2.85 (t, J=5.6 Hz, 2H), 2.15-2.01 (m, 2H).

Intermediate 1b: Synthesis of 1-(2-chloropyrimidin-4-yl)-5,6-dihydro-4H-imidazo-[4,5,1-ij]quinolin-2(1H)-one

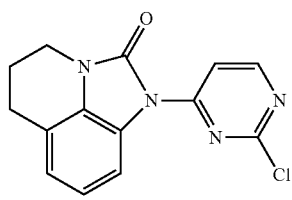

Intermediate 1b

Step 1: Synthesis of N-methoxy-3,4-dihydroquinoline-1(2H)-carboxamide

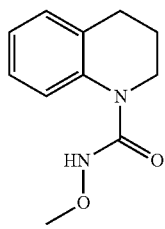

Triphosgene (335 g, 1.13 mol) was dissolved in DCM (3 L), the solution of 1,2,3,4-tetrahydroquinoline (300 g, 2.26 mol) and triethylamine (390 g, 3.86 mmol) in DCM (2 L) was added dropwise over a period of 1.5 hours between 0 to 5° C. After the addition, the mixture was stirred at room temperature for 1 hour. TLC (PE:EA=5:1) detected that most of the 1,2,3,4-tetrahydroquinoline was consumed. Triethylamine (800 g, 7.92 mol) and methoxyamine hydrochloride (375 g, 4.52 mol) were added and further stirring at room temperature (15° C.) for 16 hours. TLC (PE:EA=5:1) determined that a small portion (about 20%) of the starting material was unconsumed, then the reaction was warmed to 30° C. (water bath) for additional 3 hours. The reaction was completed determined by TLC (PE:EA=5:1), the reaction solution was washed with hydrochloric acid (2 M, 3 L), the aqueous phase extracted with DCM (1 L), combined the organic phases, washed with saturated sodium bicarbonate solution (3 L) and saturated salt solution (2 L), dried over anhydrous sodium sulfate, filtrated and dried to give the desired intermediate (580 g) as a yellow solid.

Step 2: Synthesis of 1-methoxy-5,6-dihydro-4H-imidazo[4,5,1-ij]quinolin-2(1H)-one

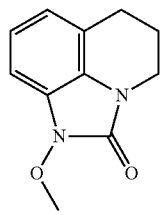

N-methoxy-3,4-dihydroquinoline-1(2H)-carboxamide (crude, 580 g, 1.13 mol) was dissolved in DCM (500 mL), the solution of bis(trifluoroacetic acid)iodobenzene (1250 g, 2.91 mol) in DCM (1.2 L) was added dropwise between −3° C. to 2° C., after the addition, naturally warmed to room temperature (15° C.) and further stirred for 1 h. The reaction was completed determined by TLC (PE:EA=1:1), saturated sodium bicarbonate solution (8 L) was added to the mixture, separated the organic phase, concentrated, the residual was purified by column chromatography (PE:EA=5:1 to 1:1) to give the desired intermediate (205 g, yield 44.5%) as a yellow solid.

Step 3: Synthesis of 5,6-dihydro-4H-imidazo[4,5,1-ij]quinolin-2(1H)-one

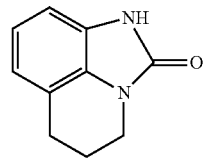 [SMILES: O=c1[nH]c2cccc3c2n1CCC3]

1-Methoxy-5,6-dihydro-4H-imidazole[4,5,1-ij]quinoline-2(1H)-one (51.25 g, 251.22 mol) was dissolved in ethanol (500 mL), raney nickel (20 g) was added at room temperature (15° C.), then the temperature was raised to 50° C. and the mixture was further stirred for 16 hours under a hydrogen balloon. TLC (PE:EA=1:1) detected that about 30% of the starting material was unconsumed. The mixture further stirred at 50° C. for 4 hours under a new hydrogen balloon, TLC (PE:EA=1:1) showed that about 20% of the starting material was still unconsumed. Additional raney nickel (8 g) was added at room temperature, and the mixture was stirred at 50° C. for 16 hours under a new hydrogen balloon. The reaction was completed determined by TLC (PE:EA=1:1). The reaction solution was cooled to room temperature, filtered through celite, the filter cake was washed three times with methanol (150 mL), and the filtrate was concentrated. The crude product (four lots combined) was slurried with PE/EA (1:1, 800 mL), filtered to afford the desired intermediate (155 g, yield 88.6%) as an off-white solid.

Step 4: Synthesis of 1-(2-chloropyrimidin-4-yl)-5,6-dihydro-4H-imidazo[4,5,1-ij]quinolin-2(1H)-one

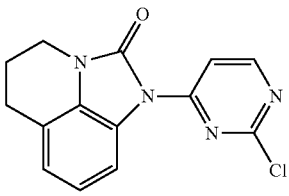

Intermediate 1b 5,6-dihydro-4H-imidazole [4,5,1-ij]quinoline-2(1H)-one (155 g, 890.80 mol) was dissolved in DMF (1.5 L), 2,4-dichloropyrimidine (158 g, 1.06 mol) and cesium carbonate (580 g, 1.78 mol) was added at room temperature (10° C.), then heated to 30° C. and further stirred for 16 hours. The reaction was completed determined by TLC (DCM:MeOH=20:1), water (3 L) was added to the reaction and further stirred for 1 hour. Filtered, the filter cake was washed with water (1 L). The filter cake was slurried with PE:EA (1:1, 1.5 L), filtered and dried to obtain the desired intermediate (230 g, yield 90.2%) as an off-white solid.

Intermediate 2a: Synthesis of N-(5-amino-2-((2-(dimethylamino)ethyl)-(methyl)-amino)-4-methoxyphenyl)acrylamide Intermediate 2a

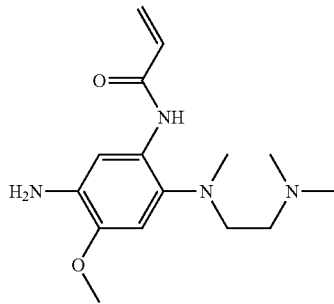

Step 1: Synthesis of $N^1$-(2-(dimethylamino)ethyl)-5-methoxy-$N^1$-methyl-2-nitrobenzene-1,4-diamine

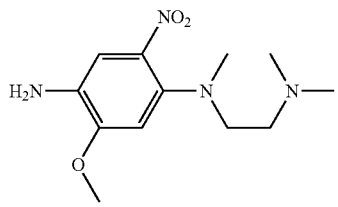 [SMILES: COc1cc(N(C)CCN(C)C)c([N+](=O)[O-])cc1N]

4-Fluoro-2-methoxy-5-nitroaniline (3 g, 16 mmol) and $N^1,N^1,N^2$-trimethylethane-1,2-diamine (2.47 g, 24 mmol) were dissolved in DMF (30 mL), potassium carbonate (4.5 g, 32 mmol) was added, stirred at 80° C. for 2 h, the reaction was completed determined by LCMS, cooled to room temperature, the mixture was diluted with water (60 mL), filtered, the filter cake was slurried with EtOH/H$_2$O (1/1), filtered and dried to obtain the desired intermediate (3.1 g) as a yellow solid; MS(ESI): m/z=269 [M+H]$^+$.

Step 2: Synthesis of tert-butyl (4-((2-(dimethylamino)ethyl)(methyl)amino)-2-methoxy-5-nitrophenyl)carbamate

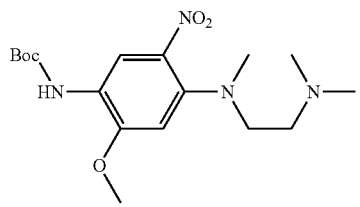 [SMILES: COc1cc(N(C)CCN(C)C)c([N+](=O)[O-])cc1NC(=O)OC(C)(C)C]

$N^1$-(2-(Dimethylamino)ethyl)-5-methoxy-$N^1$-methyl-2-nitrobenzene-1,4-diamine (3.1 g, 12 mmol) was dissolved in THF (40 mL), di-tert-butyl dicarbonate (3.8 g, 17 mmol) was added, and the mixture was stirred at 70° C. for 6 h before the reaction was completed. Then concentrated, the residual was slurried with EA/PE (1/5) to obtain the desired intermediate (3.8 g) as a pale yellow solid, MS(ESI): m/z=369 [M+H]$^+$.

Step 3: Synthesis of tert-butyl (5-amino-4-((2-(dimethylamino)ethyl)(methyl)amino)-2-methoxyphenyl) carbamate

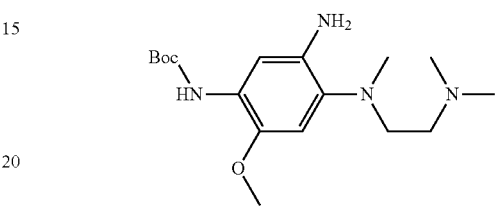

Tert-butyl (4-((2-(dimethylamino)ethyl)(methyl)amino)-2-methoxy-5-nitrophenyl) carbamate (3.8 g, 10.3 mmol) was dissolved in MeOH (40 mL), replacement with nitrogen for three times, then Pd/C (0.4 g) was added and replacement with hydrogen for three times. Then the mixture was stirred at room temperature for 4 h. After the reaction was completed, the mixture was filtered and concentrated, the crude product was directly used in the next step without further purification. MS (ESI): m/z=339 [M+H]$^+$.

Step 4: Synthesis of tert-butyl (5-acrylamido-4-((2-(dimethylamino)ethyl)(methyl)-amino)-2-methoxyphenyl)carbamate

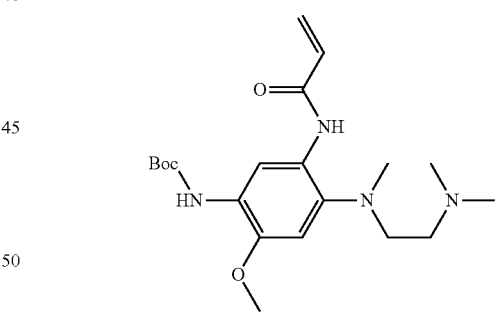

Tert-butyl (5-amino-4-((2-(dimethylamino)ethyl)(methyl)amino)-2-methoxyphenyl)-carbamate (10.3 mmol) was dissolved in DCM (50 mL), acryloyl chloride (1.36 g, 15 mmol) was sequentially added dropwise under an ice bath, then stirred for 0.5 h while naturally recovered to room temperature. The pH was adjusted to 8 by adding a saturated sodium bicarbonate solution, the aqueous phase was separated and extracted with DCM (50 mL), combined the organic phases, dried and concentrated, the residual was purified by column chromatography (MeOH/DCM=1/70 to 1/20) to give the desired intermediate (1.4 g) as a gray solid; MS (ESI): m/z=393 [M+H]$^+$.

Step 5: Synthesis of N-(5-amino-2-((2-(dimethyl-amino)ethyl)(methyl)amino)-4-methoxyphenyl)acrylamide Intermediate 2a

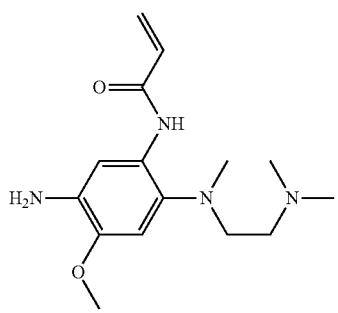

Tert-butyl (5-acrylamido-4-((2-(dimethylamino)ethyl)(methyl)amino)-2-methoxy-phenyl)-carbamate (392 mg, 1 mmol) was dissolved in DCM (5 mL), TFA (1 mL) was added dropwise, and the reaction was completed after stirring at room temperature for 1 h. The pH was adjusted to 8 by adding a saturated sodium bicarbonate solution under an ice bath. The aqueous phase was separated, extracted with DCM (50 mL), dried and concentrated, the residual was purified by column chromatography (MeOH/DCM=1/20 to 1/10) to obtain the desired intermediate (200 mg) as a brown and syrupy solid; MS (ESI): m/z=293 [M+H]$^+$.

Intermediate 2b: Synthesis of N-(5-amino-2-((2-(dimethylamino)ethyl)(methyl)-amino)-6-methoxy-pyridin-3-yl)acrylamide Intermediate 2b

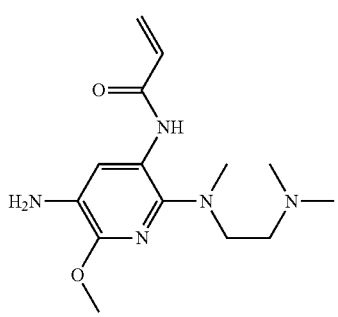

Step 1: Synthesis of 6-chloro-3-nitro-2-(2,2,2-trifluoroethoxy)pyridine

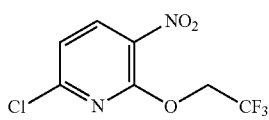

2,6-Dichloro-3-nitropyridine (500 g, 2.6 mol) was dissolved in THF (1 L), cooled to below −10° C., sodium hydrogen (104 g, 2.6 mol) was added, trifluoroethanol (260 g, 2.6 mol) was added dropwise at −15° C., after the addition, recovered the temperature to room temperature and stirred overnight. The reaction was completed determined by TLC (PE/EA=5/1), poured into iced water (1 L), stirred and separated. The organic phases were concentrated to a small volume, extracted with EA twice, combined organic phases, washed with water and saturated salt solution, dried and concentrated to give the desired intermediate (720 g) as a yellow oil-solid; MS (ESI): m/z=257 [M+H]$^+$.

Step 2: Synthesis of 6-chloro-2-(2,2,2-trifluoroethoxy)pyridin-3-amine

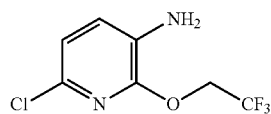 [SMILES: Nc1ccc(Cl)nc1OCC(F)(F)F]

6-Chloro-3-nitro-2-(2,2,2-trifluoroethoxy)pyridine (150 g, 0.58 mol) was dissolved in ethanol/water (1.2 L/0.3 L), ammonium chloride (160 g, 2.9 mol) was added. After the temperature was raised to 50° C. (the internal temperature), iron powder (166 g, 2.9 mol) was slowly added in batches, then stirred at 80° C. for 1 h, the reaction was completed determined by TLC (PE/EA=5/1), the temperature was reduced to 40° C. (the internal temperature), sodium carbonate (160 g) and diatomite (160 g) were added, followed by stirring for 20 min, filtrated with the aid of diatomite, the filter cake was slurried with DCM, and the ethanol-water mother solution was concentrated to dryness, which was extracted twice with the DCM in which the filter cake was slurried, the organic phases were combined, washed with water with saturated salt solution, dried and concentrated to give the desired intermediate (122 g) as black oil; MS (ESI): m/z=227 [M+H]$^+$.

Step 3: Synthesis of N-(6-chloro-2-(2,2,2-trifluoro-ethoxy)pyridin-3-yl)acetamide

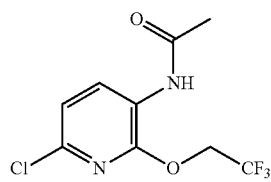 [SMILES: CC(=O)Nc1ccc(Cl)nc1OCC(F)(F)F]

6-Chloro-2-trifluoroethoxypyridine-3-amine (570 g, 2.5 mol) was dissolved in DCM (4.5 L), DIPEA (540 mL, 3.8 mol) was added. After the temperature was reduced to 0° C., acetyl chloride (200 mL, 3 mol) was added dropwise for about 1 h to maintain a the temperature around 10° C., then stirred 30 min and TLC (PE/EA=5/1) showed the reaction was completed. Water (2 L) was added under an ice bath, separated the organic phase, and the aqueous phase was extracted with DCM, combined organic phases, washed with 1 M hydrochloric acid and saturated salt solution, dried and concentrated, the residual was purified by column chromatography (PE/EA=5/1) to obtain the desired intermediate (480 g) as a yellow solid-liquid mixture; MS (ESI): m/z=269 [M+H]$^+$.

Step 4: Synthesis of N-(6-chloro-5-nitro-2-(2,2,2-trifluoroethoxy)pyridin-3-yl)acetamide

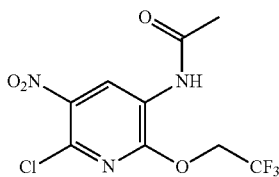

N-(6-Chloro-2-(2,2,2-trifluoroethoxy)pyridin-3-yl)acetamide (300 g, 1.1 mol) was suspended in trifluoroacetic anhydride (1.5 L) and cooled to below −5° C. Concentrated nitric acid (125 g, 1.2 mol) was added dropwise for 1 h, then stirred at −5° C. for 3 h, the reaction was completed determined by TLC (PE/EA=2/1), then added into the iced water mixture under stirring, followed by stirring a while, filtrated, the filter cake was leached with water and PE sequently, the wet product (185 g) was slurried with PE/EA (400 mL) overnight, filtered and the filter cake was slurried with PE/EA (5/1) again, filtered and dried to obtain the desired intermediate (220 g) as a yellow solid; MS (ESI): m/z=314 [M+H]$^+$.

Step 5: Synthesis of 6-chloro-5-nitro-2-(2,2,2-trifluoroethoxy)pyridin-3-amine

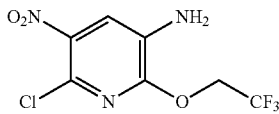

N-(6-Chloro-5-nitro-2-(2,2,2-trifluoroethoxy)pyridin-3-yl)acetamide (220 g, 0.7 mol) was suspended in a mixed solvent of methanol/concentrated hydrochloric acid (900/220 mL), heated to 50° C. for reaction about 4 h, the reaction became clear, the reaction was completed determined by TLC, added the reaction solution into water under stirring, filtrated, the filter cake was washed with water, then slurried with a saturated sodium bicarbonate solution, filtered, and the filter cake was leached with water and PE sequently, dried to obtain the desired intermediate (175 g) as a yellow solid; MS (ESI): m/z=272 [M+H]$^+$.

Step 6: Synthesis of N$^2$-(2-(dimethylamino)ethyl)-N$^2$-methyl-3-nitro-6-(2,2,2-trifluoroethoxy)pyridine-2,5-diamine

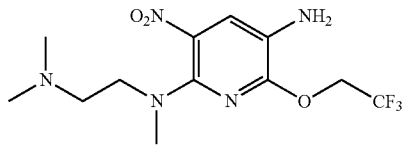 [SMILES: CN(C)CCN(C)c1nc(OCC(F)(F)F)c(N)cc1[N+](=O)[O-]]

6-Chloro-5-nitro-2-(2,2,2-trifluoroethoxy)pyridin-3-amine (950 mg, 3.5 mmol) was dissolved in acetonitrile (15 mL), K$_2$CO$_3$ (967 mg, 7 mmol) and N,N,N'-trimethylethylenediamine (643 mg, 6.3 mmol) were added at room temperature, then the reaction was stirred at 80° C. overnight. The reaction solution was filtered, the filtrate was concentrated, the residual was purified by silica gel column chromatography to obtain the desired intermediate (1.16 g) as red oil; MS (ESI): m/z=338.2 [M+H]$^+$.

Step 7: Synthesis of N$^2$-(2-(dimethylamino)ethyl)-N$^2$-methyl-3-nitro-5-di-tert-butoxycarbonylamino-6-(2,2,2-trifluoroethoxy)-2-amine

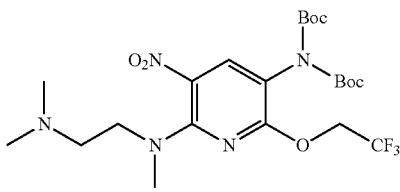

N$^2$-(2-(Dimethylamino)ethyl)-N$^2$-methyl-3-nitro-6-(2,2,2-trifluoroethoxy)pyridine-2,5-diamine (1.01 g, 3.5 mmol) and DMAP (110 mg, 0.9 mmol) were dissolved in 1,4-dioxane (30 mL), di-tert-butyl dicarbonate (1.96 g, 10.5 mmol) was added, then stirred in an oil bath at 100° C. for 8 h, concentrated, the residual was purified by column chromatography to obtain the desired intermediate (680 mg) as yellow oil; MS (ESI): m/z=538 [M+H]$^+$.

Step 8: Synthesis of N$^2$-(2-(dimethylamino)ethyl)-N$^2$-methyl-5-di-tert-butoxycarbonylamino-6-(2,2,2-trifluoroethoxy)-2,3-diamine

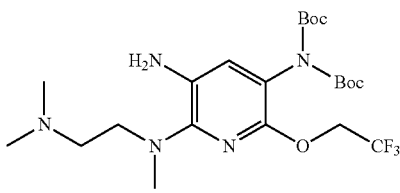 [SMILES: CN(C)CCN(C)c1nc(OCC(F)(F)F)c(N(C(=O)OC(C)(C)C)C(=O)OC(C)(C)C)cc1[N+](=O)[O-]]

N$^2$-(2-(Dimethylamino)ethyl)-N$^2$-methyl-3-nitro-5-di-tert-butoxycarbonylamino-6-(2,2,2-trifluoroethoxy)-2-amine (680 mg, 1.3 mmol) was dissolved in MeOH (30 mL), 10% Pd-C (136 mg) was added, and the air within the flask was replaced by hydrogen for three times, then stirred at room temperature for 1 h. After the reaction was completed, filtered through celite, concentrated and the residual was purified by column chromatography to obtain the desired intermediate (415 mg) as brown oil; MS (ESI): m/z=508.3 [M+H]$^+$.

Step 9: Synthesis of N-(5-di-tert-butoxycarbonylamino-2-((2-(dimethylamino)ethyl) (methyl) amino)-6-(2,2,2-trifluoroethoxy)pyridine-3-yl)acrylamide

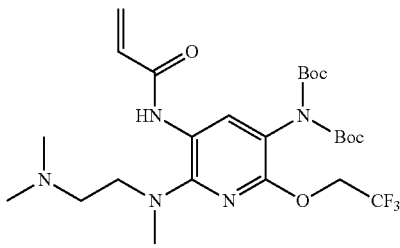 [SMILES: C=CC(=O)Nc1cc(N(C(=O)OC(C)(C)C)C(=O)OC(C)(C)C)c(OCC(F)(F)F)nc1N(C)CCN(C)C]

N²-(2-(dimethylamino)ethyl)-N²-methyl-5-di-tert-butoxycarbonylamino-6-(2,2,2-trifluoroethoxy)-2,3-diamine (415 mg, 0.8 mmol) in DCM (15 mL), triethylamine (248 mg, 2.4 mmol) was added, stirred under an ice-water bath, acryloyl chloride (148 mg, 1.6 mmol) was added dropwise, then recovered the temperature to room temperature, stirring was continued for 10 min, then quenched with water, extracted with DCM (15 mL*3), the combined organic phases were dried and concentrated, the residual was purified by column chromatography to yield the desired intermediate (318 mg) as brown oil; MS (ESI): m/z=562.3 [M+H]⁺.

Step 10: Synthesis of N-(5-amino-2-((2-(dimethylamino)ethyl)(methyl)amino)-6-methoxypyridin-3-yl)acrylamide Intermediate 2b

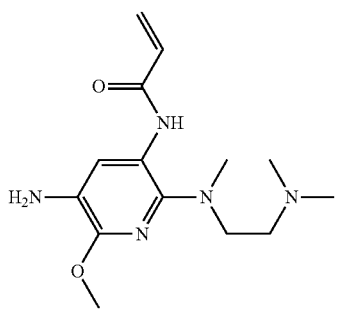

N-(5-Di-tert-butoxycarbonylamino-2-((2-(dimethylamino)ethyl) (methyl)amino)-6-(2,2,2-trifluoroethoxy)pyridine-3-yl)acrylamide (318 mg, 0.57 mmol) was dissolved in DCM (20 mL), methanesulfonic acid (1.63 g, 5.7 mmol) was added dropwise under an ice-water bath, then stirring continued for 2.5 h after the temperature naturally recovered to room temperature. Gradually adjusted the pH to 8 by dropwise addition of saturated sodium bicarbonate solution under an ice-water bath, extracted with DCM (25 mL*3), combined the organic phases, dried and concentrated, the residual was purified by column chromatography to obtain the desired intermediate (176 mg) as a pale brownish-green solid; MS (ESI): m/z=362.2 [M+H]⁺.

Example1: Synthesis of N-(2-((2-(dimethylamino)ethyl)(methyl)amino)-5-((4-(8-fluoro-2-oxo-5,6-dihydro-4H-imidazo[4,5,1-ij]quinolin-1(2H)-yl)pyrimidin-2-yl)amino)-4-methoxyphenyl)acrylamide

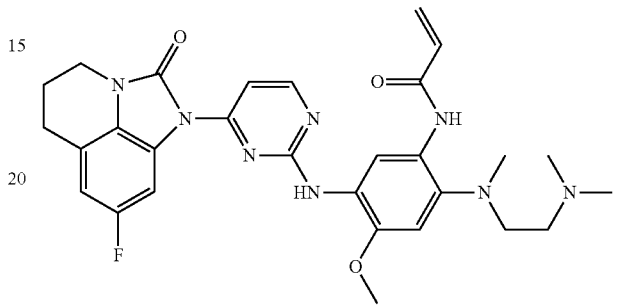

Intermediate 1a (152 mg, 0.2 mmol), intermediate 2a (200 mg, 0.68 mmol), palladium acetate (45 mg, 0.2 mmol), Xanphos (116 mg, 0.2 mmol) and cesium carbonate (130 mg, 0.4 mmol) were added to 1,4-dioxane (5 mL) with stirring at 90° C. for 10 h. After the reaction was completed, filtered through celite, concentrated and the residual was purified by column chromatography (MeOH/DCM=1/10) to give desired target compound (41 mg) as a pale brown solid.

The compounds synthesized in the same method are shown in the following table:

TABLE 2

| No | Structure | Name | ¹HNMR and MS |
|---|---|---|---|
| 1 | 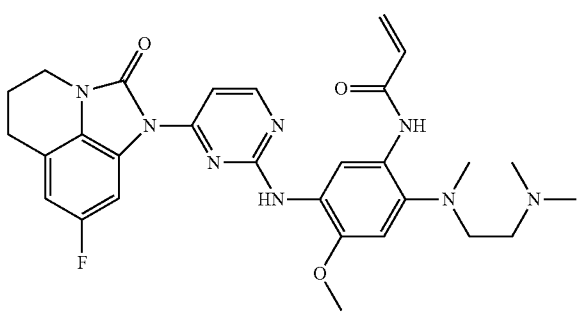 [SMILES: C=CC(=O)Nc1cc(Nc2nccc(-n3c(=O)n4c5c(cc(F)cc53)CCC4)n2)c(OC)cc1N(C)CCN(C)C] | N-(2-((2-(dimethylamino)ethyl)(methyl)amino)-5-((4-(8-fluoro-2-oxo-5,6-dihydro-4H-imidazo[4,5,1-ij]quinolin-1(2H)-yl)pyrimidin-2-yl)amino)-4-methoxyphenyl)acrylamide | MS (ESI): m/z = 562.3 [M + H]⁺, ¹H NMR (400 MHz, DMSO-d₆) δ 9.82 (s, 1H), 8.95 (s, 1H), 8.39 (d, J = 5.6 Hz, 1H), 8.10 (s, 1H), 7.72 (d, J = 5.6 Hz, 2H), 6.85 (d, J = 9.8 Hz, 1H), 6.44 (dd, J = 17.0, 10.2 Hz, 1H), 6.19 (d, J = 17.5 Hz, 1H), 5.80-5.65 (m, 1H), 3.94-3.66 (m, 5H), 3.18 (t, J = 6.3 Hz, 2H), 2.87 (s, 3H), 2.79 (t, J = 5.2 Hz, 2H), 2.50 (s, 2H), 2.20 (s, 6H), 2.08-1.95 (m, 2H). |
| 2 | 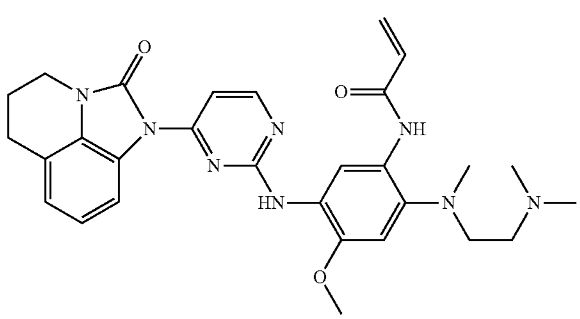 | N-(2-((2-(dimethylamino)ethyl)(methyl)amino)-4-methoxy-5-((4-(2-oxo-5,6-dihydro-4H-imidazo[4,5,1-ij]quinolin-1(2H)-yl)pyrimidin-2-yl)amino)phenyl)acrylamide | MS (ESI): m/z = 543.3 [M + H]⁺, ¹H NMR (400 MHz, DMSO-d₆) δ 10.08 (s, 1H), 8.70 (s, 1H), 8.46-8.35 (m, 2H), 7.77 (m, 1H), 7.71 (d, J = 5.6 Hz, 1H), 7.04 (s, 1H), 6.92 (d, J = 7.6 Hz, 1H), 6.77 (t, J = 7.9 Hz, 1H), 6.38 (dd, J = 16.9, 10.1 Hz, 1H), 6.17 (dd, J = 16.9, 1.9 Hz, 1H), 5.71 (dd, J = 10.1, 1.9 Hz, 1H), 3.77 (t, J = 5.6 Hz, 2H), 3.73 (s, 3H), 2.90 (t, J = 5.7 Hz, 2H), 2.78 t, J = 5.6 Hz, 2H), 2.74 (s, 3H), 2.33 (t, J = 5.6 Hz, 2H), 2.20 (s, 6H), 2.05-1.97 (m, 2H). |

TABLE 2-continued

| No | Structure | Name | ¹HNMR and MS |
|---|---|---|---|
| 3 | 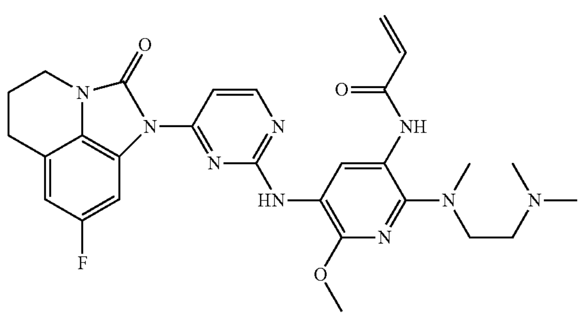 | N-(2-((2-(dimethylamino) ethyl)(methyl) amino)-5-((4-(8-fluoro-2-oxo-5,6-dihydro-4H-imidazo[4,5,1-ij]quinolin-1(2H)-yl)pyrimidin-2-yl)amino)-6-methoxypyridin-3-yl)acrylamide | MS (ESI): m/z = 562.3 [M + H]⁺, ¹H NMR (400 MHz, DMSO-d₆) δ 9.82 (s, 1H), 8.95 (s, 1H), 8.39 (d, J = 5.6 Hz, 1H), 8.10 (s, 1H), 7.72 (d, J = 5.6 Hz, 2H), 6.85 (d, J = 9.8 Hz, 1H), 6.44 (dd, J = 17.0, 10.2 Hz, 1H), 6.19 (d, J = 17.5 Hz, 1H), 5.80-5.65 (m, 1H), 3.94-3.66 (m, 5H), 3.18 (t, J = 6.3 Hz, 2H), 2.87 (s, 3H), 2.79 (t, J = 5.2 Hz, 2H), 2.50 (s, 2H), 2.20 (s, 6H), 2.08-1.95 (m, 2H). |
| 4 | 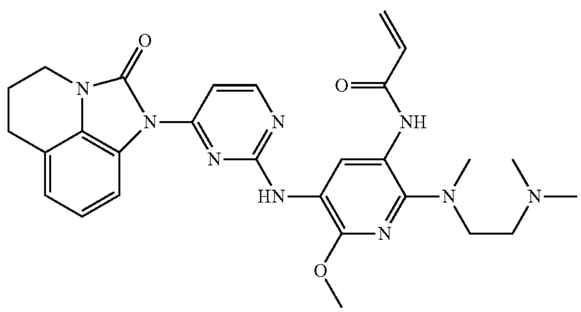 | N-(2-((2-(dimethylamino) ethyl)(methyl) amino)-6-methoxy-5-((4-(2-oxo-5,6-dihydro-4H-imidazo[4,5,1-ij]quinolin-1(2H)-yl)pyrimidin-2-yl)amino)pyridin-3-yl)acrylamide | MS (ESI): m/z = 544.3 [M + H]⁺, ¹H NMR (400 MHz, CDCl₃) δ 10.06 (s, 1H), 9.55 (s, 1H), 8.51 (d, J = 5.7 Hz, 1H), 8.06 (d, J = 7.9 Hz, 1H), 7.86 (d, J = 5.7 Hz, 1H), 7.26 (s, 1H), 7.00 (t, J = 7.8 Hz, 1H), 6.94 (d, J = 7.3 Hz, 1H), 6.43-6.27 (m, 2H), 5.72-5.62 (m, 1H), 3.99 (s, 3H), 3.93-3.86 (m, 2H), 3.03 (s, 2H), 2.88 (t, J = 6.0 Hz, 2H), 2.77 (s, 3H), 2.45 (s, 2H), 2.37 (s, 6H), 2.14 (dt, J = 11.7, 6.0 Hz, 2H). |
| 5 | 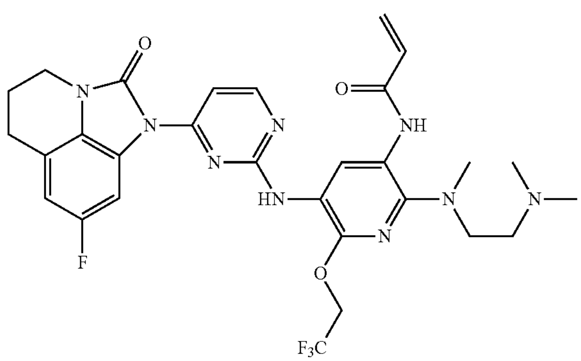 | N-(2-((2-(dimethylamino) ethyl)(methyl) amino)-5-((4-(8-fluoro-2-oxo-5,6-dihydro-4H-imidazo[4,5,1-ij]quinolin-1(2H)-yl)pyrimidin-2-yl)amino)-6-(2,2,2-trifluoroethoxy)pyridin-3-yl)acrylamide | MS (ESI): m/z = 630.3 [M + H]⁺, ¹H NMR (400 MHz, DMSO-d₆) δ 9.90 (s, 1H), 9.04 (s, 1H), 8.39 (d, J = 5.6 Hz, 1H), 8.06 (s, 1H), 7.73 (d, J = 5.7 Hz, 1H), 7.56 (s, 1H), 6.85 (d, J = 9.2 Hz, 1H), 6.44 (dd, J = 16.9, 10.2 Hz, 1H), 6.21 (d, J = 16.7 Hz, 1H), 5.74 (d, J = 11.1 Hz, 1H), 4.90 (q, J = 8.9 Hz, 2H), 3.77 (t, J = 5.5 Hz, 2H), 3.20 (t, J = 6.4 Hz, 2H), 2.88 (s, 3H), 2.79 (t, J = 5.3 Hz, 2H), 2.47 (s, 2H), 2.20 (s, 6H), 2.09-1.96 (m, 2H). |
| 6 | 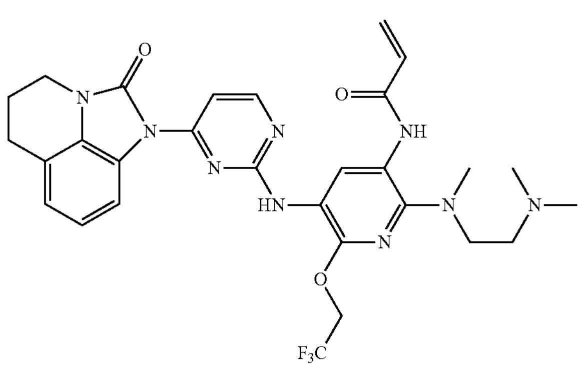 [SMILES: C=CC(=O)Nc1cc(Nc2nccc(-n3c(=O)n4c5c(cccc53)CCC4)n2)c(OCC(F)(F)F)nc1N(C)CCN(C)C] | N-(2-((2-(dimethylamino) ethyl)(methyl) amino)-5-((4-(2-oxo-5,6-dihydro-4H-imidazo[4,5,1-ij]quinolin-1(2H)-yl)pyrimidin-2-yl)amino)-6-(2,2,2-trifluoroethoxy)pyridin-3-yl)acrylamide | MS (ESI): m/z = 612.3 [M + H]⁺, ¹H NMR (400 MHz, DMSO-d₆) δ 9.83 (s, 1H), 9.13 (s, 1H), 9.01 (s, 1H), 8.38 (d, J = 5.7 Hz, 1H), 7.88 (s, 1H), 7.75 (d, J = 5.8 Hz, 2H), 6.95 (d, J = 7.4 Hz, 1H), 6.84 (s, 1H), 6.52 (dd, J = 17.0, 10.2 Hz, 1H), 6.28 (d, J = 17.1 Hz, 1H), 5.79 (d, J = 11.9 Hz, 1H), 4.91 (q, J = 9.0 Hz, 2H), 3.81-3.75 (m, 2H), 3.68 (t, J = 6.5 Hz, 2H), 3.30 (d, J = 5.5 Hz, 2H), 2.85-2.77 (m, 11H), 2.31 (s, 3H), 2.01 (s, 2H). |

TABLE 2-continued

| No | Structure | Name | ¹HNMR and MS |
|---|---|---|---|
| 7 | 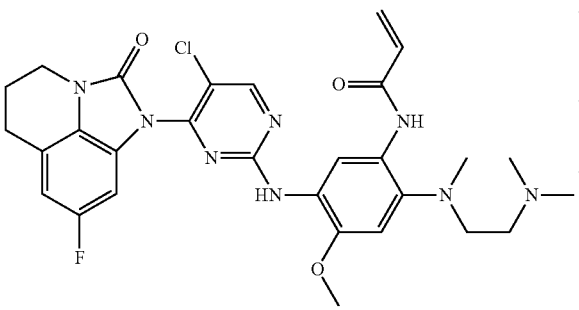 [SMILES: C=CC(=O)Nc1cc(Nc2ncc(Cl)c(-n3c(=O)n4c5c(cc(F)cc53)CCC4)n2)c(OC)cc1N(C)CCN(C)C] | N-(5-((5-chloro-4-(8-fluoro-2-oxo-5,6-dihydro-4H-imidazo[4,5,1-ij]quinolin-1(2H)-yl)pyrimidin-2-yl)amino)-2-((2-(dimethylamino)ethyl)(methyl)amino)-4-methoxyphenyl)acrylamide | MS (ESI): m/z = 595.4 [M + H]⁺, ¹H NMR (400 MHz, DMSO-d₆) δ 10.11 (s, 1H), 8.89 (s, 1H), 8.38 (s, 1H), 7.62 (s, 1H), 7.42 (s, 1H), 7.00 (s, 1H), 6.79 (d, J = 10.0 Hz, 1H), 6.46-6.06 (m, 3H), 5.70 (d, J = 10.2 Hz, 1H), 3.74 (s, 5H), 2.87 (s, 2H), 2.73 (s, 5H), 2.31 (s, 2H), 2.17 (s, 6H), 1.99 (s, 2H). |
| 8 | 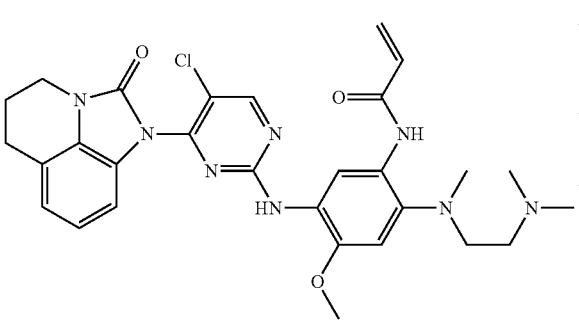 | N-(5-((5-chloro-4-(2-oxo-5,6-dihydro-4H-imidazo[4,5,1-ij]quinolin-1(2H)-yl)pyrimidin-2-yl)amino)-2-((2-(dimethylamino)ethyl)(methyl)amino)-4-methoxyphenyl)acrylamide | MS (ESI): m/z = 577.3 [M + H]⁺, ¹H NMR (400 MHz, DMSO-d₆) δ 10.08 (s, 1H), 8.71 (s, 1H), 8.46-8.36 (m, 2H), 7.79 (m, 1H), 7.4 (s, 1H), 7.04 (s, 1H), 6.78 (t, J = 7.9 Hz, 1H), 6.38 (dd, J = 16.9, 10.1 Hz, 1H), 6.17 (dd, J = 16.9, 1.9 Hz, 1H), 5.71 (dd, J = 10.1, 1.9 Hz, 1H), 3.78 (t, J = 5.6 Hz, 2H), 3.75 (s, 3H), 2.91 (t, J = 5.7 Hz, 2H), 2.79 (t, J = 5.6 Hz, 2H), 2.72 (s, 3H), 2.31 (t, J = 5.6 Hz, 2H), 2.21 (s, 6H), 2.05-1.99 (m, 2H). |
| 9 | 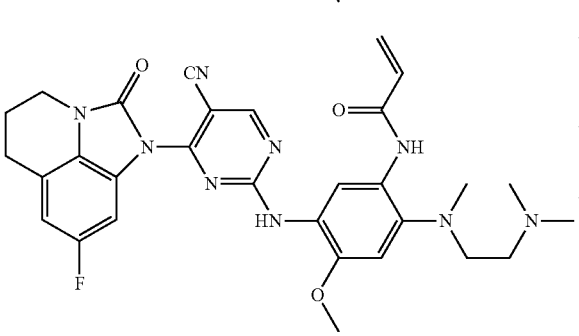 | N-(5-((5-cyano-4-(8-fluoro-2-oxo-5,6-dihydro-4H-imidazo[4,5,1-ij]quinolin-1(2H)-yl)pyrimidin-2-yl)amino)-2-((2-(dimethylamino)ethyl)(methyl)amino)-4-methoxyphenyl)acrylamide | MS (ESI): m/z = 586.3 [M + H]⁺, ¹H NMR (400 MHz,DMSO-d₆) δ 10.04 (s, 1H), 8.89 (s, 1H), 8.40 (s, 2H), 7.61 (s, 1H), 7.40 (s, 1H), 7.01 (s, 1H), 6.77 (d, J = 10.0 Hz, 1H), 6.46-6.05 (m, 3H), 5.71 (d, J = 10.2 Hz, 1H), 3.78 (s, 5H), 2.88 (s, 2H), 2.72 (s, 5H), 2.30 (s, 2H), 2.18 (s, 6H), 1.98 (s, 2H). |
| 10 | 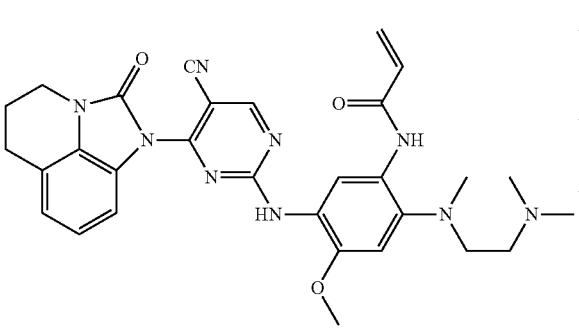 [SMILES: C=CC(=O)Nc1cc(Nc2ncc(C#N)c(-n3c(=O)n4c5c(cccc53)CCC4)n2)c(OC)cc1N(C)CCN(C)C] | N-(5-((5-cyano-4-(2-oxo-5,6-dihydro-4H-imidazo[4,5,1-ij]quinolin-1(2H)-yl)pyrimidin-2-yl)amino)-2-((2-(dimethylamino)ethyl)(methyl)amino)-4-methoxyphenyl)acrylamide | MS (ESI): m/z = 568.3 [M + H]⁺, ¹H NMR (400 MHz, CDCl₃) δ 10.05 (s, 1H), 8.40 (s, 1H), 7.39 (dd, J = 14.8, 3.1 Hz, 1H), 7.12 (s, 1H), 6.85 (t, J = 14.8 Hz, 1H), 6.71 (dd, J = 14.8, 3.2 Hz, 1H), 6.43 (s, 1H), 6.22 (dd, J = 32.8, 20.0 Hz, 1H), 6.05 (dd, J = 20.0, 5.1 Hz, 1H), 5.69 (dd, J = 32.8, 5.1 Hz, 1H), 5.05 (s, 1H), 3.86 (s, 3H), 3.65-3.55 (m, 3H), 3.50 (t, J = 14.4 Hz, 1H), 2.79 (t, J = 12.0 Hz, 2H), 2.75 (s, 3H), 2.50 (t, J = 14.4 Hz, 2H), 2.21 (s, 6H), 1.62 (p, J = 11.4 Hz, 2H). |
| 11 | 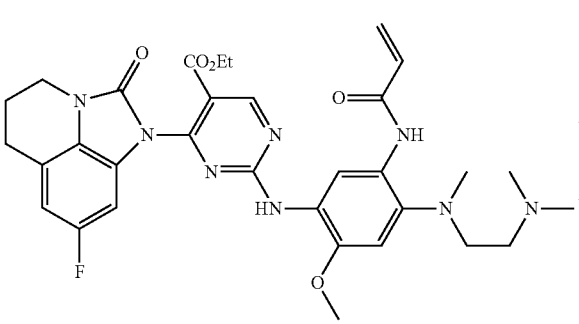 | ethyl 2-((5-acrylamido-4-((2-(dimethylamino)ethyl)(methyl)amino)-2-methoxyphenyl)amino)-4-(8-fluoro-2-oxo-5,6-dihydro-4H-imidazo[4,5,1-ij]quinolin-1(2H)-yl)pyrimidine-5-carboxylate | MS (ESI): m/z = 633.4 [M + H]⁺, ¹H NMR (400 MHz, CDCl₃) δ 10.01 (s, 1H), 7.55 (s, 1H), 7.44 (dd, J = 15.8, 3.0 Hz, 1H), 7.08 (s, 1H), 6.75 (dd, J = 15.8, 3.0 Hz, 1H), 6.39 (s, 1H), 6.15 (dd, J = 32.3, 19.8 Hz, 1H), 6.01 (dd, J = 20.0, 5.5 Hz, 1H), 5.65 (dd, J = 32.4, 5.4 Hz, 1H), 5.06 (s, 1H), 4.21 (q, J = 11.8 Hz, 2H), 3.84 (s, 3H), 3.54 (dt, J = 29.8, 13.0 Hz, 4H), 2.87-2.68 (m, 5H), 2.48 (t, J = 14.4 Hz, 2H), 2.20 (s, 6H), 1.61 (p, J = 11.4 Hz, 2H), 1.29 (t, J = 11.8 Hz, 3H). |

TABLE 2-continued

| No | Structure | Name | ¹HNMR and MS |
|---|---|---|---|
| 12 | 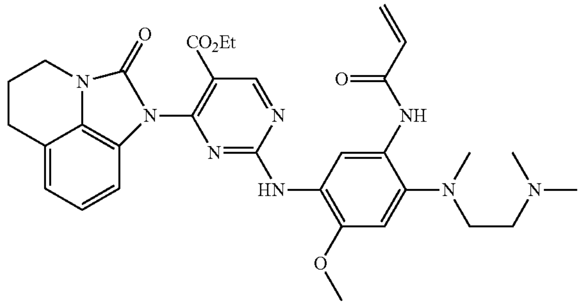 | ethyl 2-((5-acrylamido-4-((2-(dimethylamino)ethyl)(methyl)amino)-2-methoxyphenyl)amino)-4-(2-oxo-5,6-dihydro-4H-imidazo[4,5,1-ij]quinolin-1(2H)-yl)pyrimidine-5-carboxylate | MS (ESI): m/z = 615.4 [M + H]⁺, ¹H NMR (400 MHz, CDCl₃) δ 10.10 (s, 1H), 7.60 (s, 1H), 7.39 (dd, J = 14.8, 3.2 Hz, 1H), 7.12 (s, 1H), 6.85 (t, J = 14.8 Hz, 1H), 6.71 (dd, J = 14.8, 3.2 Hz, 1H), 6.43 (s, 1H), 6.20 (dd, J = 32.6, 19.9 Hz, 1H), 6.05 (dd, J = 20.0, 5.3 Hz, 1H), 5.69 (dd, J = 32.6, 5.3 Hz, 1H), 5.08 (s, 1H), 4.24 (q, J = 11.8 Hz, 2H), 3.86 (s, 3H), 3.67-3.43 (m, 4H), 2.85-2.70 (m, 5H), 2.50 (t, J = 14.6 Hz, 2H), 2.21 (s, 6H), 1.73-1.54 (m, 2H), 1.30 (t, J = 11.8 Hz, 3H). |
| 13 | 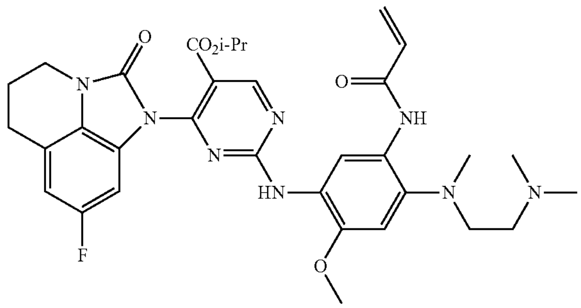 | isopropyl 2-((5-acrylamido-4-((2-(dimethylamino)ethyl)(methyl)amino)-2-methoxyphenyl)amino)-4-(8-fluoro-2-oxo-5,6-dihydro-4H-imidazo[4,5,1-ij]quinolin-1(2H)-yl)pyrimidine-5-carboxylate | MS (ESI): m/z = 647.5 [M + H]⁺, ¹H NMR (400 MHz, DMSO-d₆) δ 10.05 (s, 1H), 9.24 (s, 1H), 8.96 (s, 1H), 8.41 (s, 1H), 8.13 (s, 1H), 7.75 (d, J = 5.7 Hz, 2H), 7.02 (s, 1H), 6.85 (d, J = 8.3 Hz, 1H), 6.66 (dd, J = 16.9, 10.3 Hz, 1H), 6.24 (dd, J = 17.0, 1.8 Hz, 1H), , 5.10 (m, 1H) 3.84-3.71 (m, 5H), 3.30 (s, 4H), 2.80 (dd, J = 16.5, 5.4 Hz, 8H), 2.63 (s, 3H), 2.33 (s, 3H), 2.07-1.98 (m, 2H), 1.42 (d, 6H). |
| 14 | 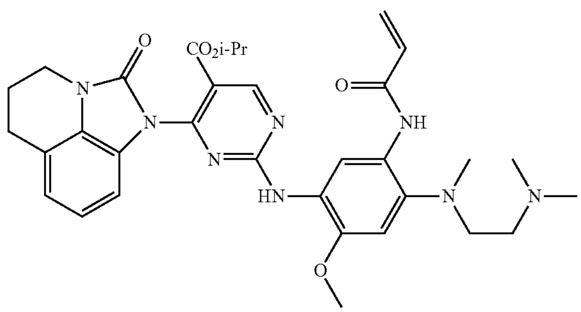 | isopropyl 2-((5-acrylamido-4-((2-(dimethylamino)ethyl)(methyl)amino)-2-methoxyphenyl)amino)-4-(2-oxo-5,6-dihydro-4HI-imidazo[4,5,1-ij]quinolin-1(2H)-yl)pyrimidine-5-carboxylate | MS (ESI): m/z = 629.4 [M + H]⁺, ¹H NMR (400 MHz, DMSO-d₆) δ 10.08 (s, 1H), 8.70 (s, 1H), 8.46-8.35 (m, 2H), 7.77 (m, 1H), 7.50 (s, 1H), 7.04 (s, 1H),, 6.77 (t, J = 7.9 Hz, 1H), 6.38 (dd, J = 16.9, 10.1 Hz, 1H), 6.17 (dd, J = 16.9, 1.9 Hz, 1H), 5.71 (dd, J = 10.1, 1.9 Hz, 1H), 5.05 (m, 1H),3.75 (t, J = 5.6 Hz, 2H), 3.71 (s, 3H), 2.91 (t, J = 5.7 Hz, 2H), 2.77 (t, J = 5.6 Hz, 2H), 2.75 (s, 3H), 2.30 (t, J = 5.6 Hz, 2H), 2.19 (s, 6H), 1.40 (d, 6H). |
| 15 | 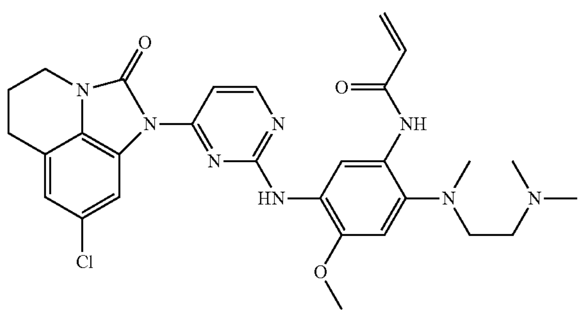 | N-(5-((4-(8-chloro-2-oxo-5,6-dihydro-4H-imidazo[4,5,1-ij]quinolin-1(2H)-yl)pyrimidin-2-yl)amino)-2-((2-(dimethylamino)ethyl)(methyl)amino)-4-methoxyphenyl)acrylamide | MS (ESI): m/z = 577.4 [M + H]⁺, ¹H NMR (400 MHz, DMSO-d₆) δ 10.05 (s, 1H), 9.01 (s, 1H), 8.96 (s, 1H), 8.45 (d, J = 5.7 Hz, 1H), 8.13 (s, 1H), 7.75 (d, J = 5.7 Hz, 1H), 7.30 (s, 1H), 7.05 (s, 1H), 6.66 (dd, J = 16.9, 10.3 Hz, 1H), 6.24 (dd, J = 17.0, 1.8 Hz, 1H), 5.76 (d, J = 11.9 Hz, 1H), 3.84-3.71 (m, 5H), 3.30 (s, 4H), 2.80 (dd, J = 16.5, 5.4 Hz, 8H), 2.63 (s, 3H), 2.33 (s, 3H), 2.07-1.98 (m, 2H). |
| 16 | 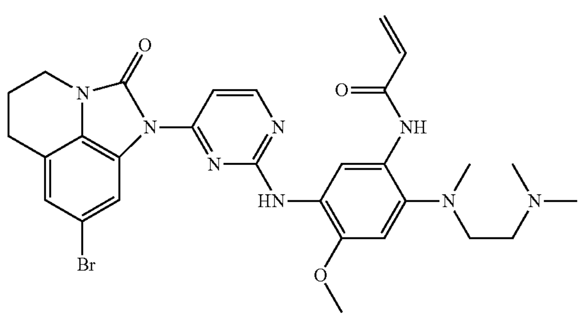 | N-(5-((4-(8-bromo-2-oxo-5,6-dihydro-4H-imidazo[4,5,1-ij]quinolin-1(2H)-yl)pyrimidin-2-yl)amino)-2-((2-(dimethylamino)ethyl)(methyl)amino)-4-methoxyphenyl)acrylamide | MS (ESI): m/z = 621.3 [M + H]⁺, ¹H NMR (400 MHz, DMSO-d₆) δ 10.12 (s, 1H), 9.09 (s, 1H), 8.80 (s, 1H), 8.40 (d, J = 5.7 Hz, 1H), 8.02 (s, 1H), 7.73 (d, J = 5.7 Hz, 1H), 7.30 (s, 1H), 7.08 (s, 1H), 6.38 (dd, J = 16.9, 10.1 Hz, 1H), 6.17 (dd, J = 16.9, 1.9 Hz, 1H), 5.71 (dd, J = 10.1, 1.9 Hz, 1H), 3.78 (t, J = 5.6 Hz, 2H), 3.73 (s, 3H), 2.90 (t, J = 5.7 Hz, 2H), 2.80 (t, J = 5.6 Hz, 2H), 2.74 (s, 3H), 2.33 (t, J = 5.6 Hz, 2H), 2.19 (s, 6H). |

TABLE 2-continued

| No | Structure | Name | ¹HNMR and MS |
|----|-----------|------|--------------|
| 17 | 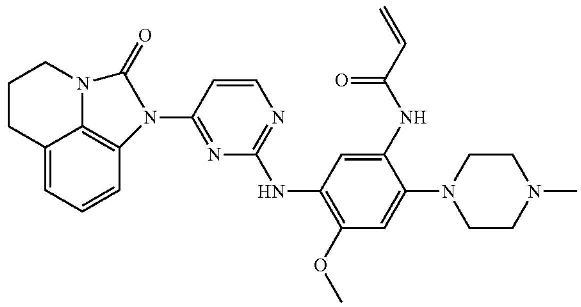 [SMILES: C=CC(=O)Nc1cc(Nc2nccc(-n3c(=O)n4c5c(cccc53)CCC4)n2)c(OC)cc1N1CCN(C)CC1] | N-(4-methoxy-2-(4-methylpiperazin-1-yl)-5-((4-(2-oxo-5,6-dihydro-4H-imidazo[4,5,1-ij]quinolin-1(2H)-yl)pyrimidin-2-yl)amino)phenyl)acrylamide | MS (ESI): m/z = 541.4 [M + H]⁺, ¹H NMR (400 MHz, DMSO-d₆) δ 10.08 (s, 1H), 8.70 (s, 1H), 8.46-8.35 (m, 2H), 7.77 (m, 1H), 7.71 (d, J = 5.6 Hz, 1H), 7.04 (s, 1H), 6.92 (d, J = 7.6 Hz, 1H), 6.77 (t, J = 7.9 Hz, 1H), 6.38 (dd, J = 16.9, 10.1 Hz, 1H), 6.17 (dd, J = 16.9, 1.9 Hz, 1H), 5.71 (dd, J = 10.1, 1.9 Hz, 1H), 3.79 (t, J = 5.6 Hz, 2H), 3.74 (s, 3H), 2.89 (t, J = 5.7 Hz, 2H), 2.78 (t, J = 5.6 Hz, 4H), 2.31 (t, J = 5.6 Hz, 4H), 2.20 (s, 3H). |
| 18 | 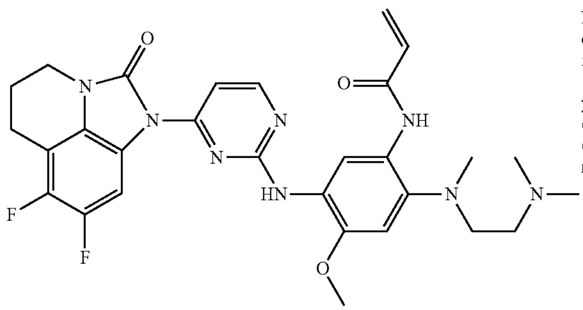 | N-(5-((4-(7,8-difluoro-2-oxo-5,6-dihydro-4H-imidazo[4,5,1-ij]quinolin-1(2H)-yl)pyrimidin-2-yl)amino)-2-((2-(dimethylamino)ethyl)(methyl)amino)-4-methoxyphenyl)acrylamide | MS (ESI): m/z = 579.3 [M + H]⁺, ¹H NMR (400 MHz, DMSO-d₆) δ 10.08 (s, 1H), 8.87 (s, 1H), 8.51 (d, J = 5.7 Hz, 1H), 7.90 (m, 1H), 7.86 (d, J = 5.7 Hz, 1H), 7.61 (s, 1H), 7.01 (s, 1H), 6.45-6.06 (m, 2H), 5.69 (d, J = 10.2 Hz, 1H), 3.72 (s, 5H), 2.85 (s, 2H), 2.72 (s, 5H), 2.32 (s, 2H), 2.19 (s, 6H), 1.98 (s, 2H). |
| 19 | 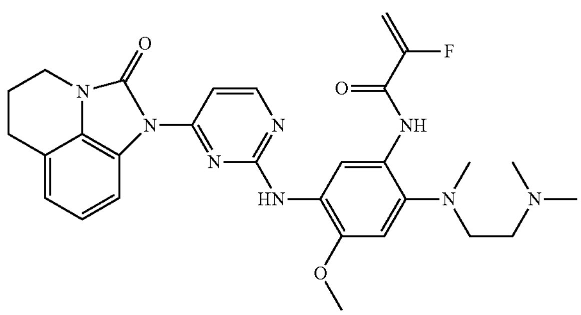 [SMILES: C=C(F)C(=O)Nc1cc(Nc2nccc(-n3c(=O)n4c5c(cccc53)CCC4)n2)c(OC)cc1N(C)CCN(C)C] | N-(2-((2-(dimethylamino)ethyl)(methyl)amino)-4-methoxy-5-((4-(2-oxo-5,6-dihydro-4H-imidazo[4,5,1-ij]quinolin-1(2H)-yl)pyrimidin-2-yl)amino)phenyl)-2-fluoroacrylamide | MS (ESI): m/z = 561.3 [M + H]⁺, ¹H NMR (400 MHz, DMSO-d₆) δ 10.01 (s, 1H), 8.59 (s, 1H), 8.53-8.31 (m, 2H), 7.87 (m, 1H), 7.74 (d, J = 4.8 Hz, 1H), 7.12 (s, 1H), 6.98 (d, J = 7.6 Hz, 1H), 6.53 (t, J = 7.7 Hz, 1H), 5.88 (d, J = 4.3 Hz, 0.5H), 5.72 (d, J = 4.2 Hz, 0.5H), 5.69 (d, J = 4.2 Hz, 0.5H), 5.4 (d, J = 4.1 Hz, 0.5H), 3.57 (t, J = 5.6 Hz, 2H), 3.43 (s, 3H), 2.93 (t, J = 5.2 Hz, 2H), 2.79 (t, J = 5.2 Hz, 2H), 2.72 (s, 3H), 2.32 (t, J = 5.3 Hz, 2H), 2.20 (s, 6H), 2.10-1.95 (m, 2H). |
| 20 | 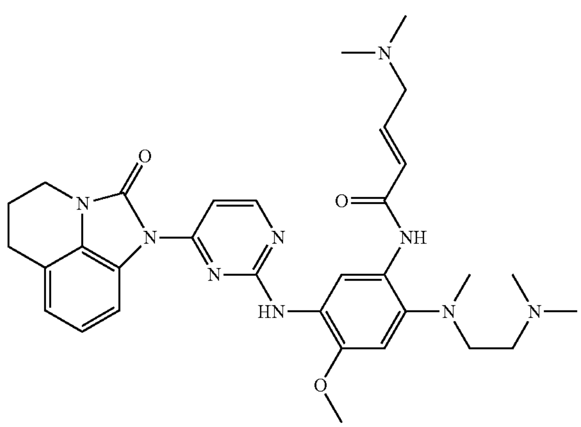 [SMILES: COc1cc(N(C)CCN(C)C)c(NC(=O)/C=C/CN(C)C)cc1Nc1nccc(-n2c(=O)n3c4c(cccc42)CCC3)n1] | (E)-4-(dimethylamino)-N-(2-((2-(dimethylamino)ethyl)(methyl)amino)-4-methoxy-5-((4-(2-oxo-5,6-dihydro-4H-imidazo[4,5,1-ij]quinolin-1(2H)-yl)pyrimidin-2-yl)amino)phenyl)but-2-enamide | MS (ESI): m/z = 600.4 [M + H]⁺, ¹H NMR (400 MHz, DMSO-d₆) δ 10.06 (s, 1H), 8.71 (s, 1H), 8.33 (d, J = 5.4 Hz, 1H), 8.22 (s, 1H), 7.72 (s, 1H), 7.66 (d, J = 5.7 Hz, 1H), 7.01 (s, 1H), 6.92 (d, J = 7.3 Hz, 1H), 6.81 (t, J = 7.5 Hz, 1H), 6.35 (d, J = 10.3 Hz, 1H), 5.98-6.12 (m, 1H), 3.87 (t, J = 5.4 Hz, 2H), 3.71 (s, 3H), 3.02 (d, J = 5.6 Hz, 2H) 2.91 (t, J = 5.7 Hz, 2H), 2.76 (t, J = 5.4 Hz, 2H), 2.72 (s, 3H), 2.53 (t, J = 5.5 Hz, 2H), 2.12 (s, 6H), 2.16 (s, 6H), 2.07-1.98 (m, 2H). |

TABLE 2-continued

| No | Structure | Name | ¹HNMR and MS |
|---|---|---|---|
| 21 | 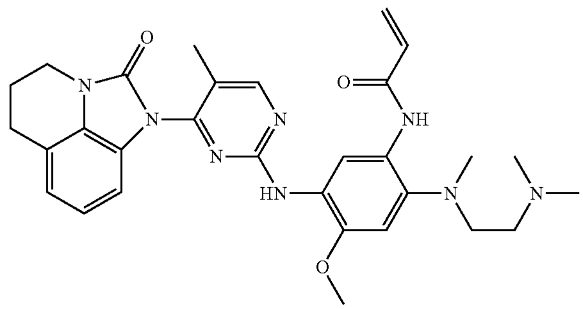 [SMILES: C=CC(=O)Nc1cc(Nc2ncc(C)c(-n3c(=O)n4c5c(cccc53)CCC4)n2)c(OC)cc1N(C)CCN(C)C] | N-(2-((2-(dimethylamino)ethyl)(methyl)amino)-4-methoxy-5-((5-methyl-4-(2-oxo-5,6-dihydro-4H-imidazo[4,5,1-ij]quinolin-1(2H)-yl)pyrimidin-2-yl)amino)phenyl)acrylamide | MS (ESI): m/z = 557.3 [M + H]⁺, ¹H NMR (400 MHz, DMSO-d₆) δ 10.18 (s, 1H), 8.74 (s, 1H), 8.48-8.31 (m, 2H), 7.87 (m, 1H), 7.02 (s, 1H), 6.90 (d, J = 7.4 Hz, 1H), 6.77 (t, J = 7.7 Hz, 1H), 6.35 (dd, J = 16.1, 10.0 Hz, 1H), 6.15 (dd, J = 16.2, 1.8 Hz, 1H), 5.70 (dd, J = 10.7, 1.7 Hz, 1H), 3.77 (t, J = 5.5 Hz, 2H), 3.75 (s, 3H), 2.92 (t, J = 5.5 Hz, 2H), 2.78 (t, J = 5.2 Hz, 2H), 2.74 (s, 3H), 2.33 (t, J = 5.2 Hz, 2H), 2.24 (s, 6H), 2.01-1.87 (m, 2H). |
| 22 | 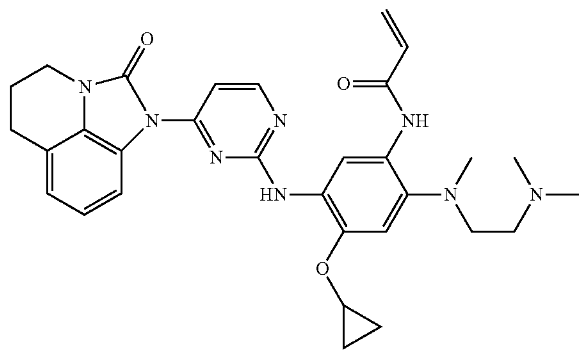 [SMILES: C=CC(=O)Nc1cc(Nc2nccc(-n3c(=O)n4c5c(cccc53)CCC4)n2)c(OC2CC2)cc1N(C)CCN(C)C] | N-(4-cyclopropoxy-2-((2-(dimethylamino)ethyl)(methyl)amino)-5-((4-(2-oxo-5,6-dihydro-4H-imidazo[4,5,1-ij]quinolin-1(2H)-yl)pyrimidin-2-yl)amino)phenyl)acrylamide | MS (ESI): m/z = 569.5 [M + H]⁺, ¹H NMR (400 MHz, DMSO-d₆) δ 10.10 (s, 1H), 8.72 (s, 1H), 8.48-8.38 (m, 2H), 7.79 (m, 1H), 7.72 (d, J = 5.6 Hz, 1H), 7.05 (s, 1H), 6.94 (d, J = 7.6 Hz, 1H), 6.78 (t, J = 7.9 Hz, 1H), 6.40 (dd, J = 16.9, 10.1 Hz, 1H), 6.18 (dd, J = 16.9, 1.9 Hz, 1H), 5.71 (dd, J = 10.1, 1.9 Hz, 1H), 3.74 (t, J = 5.6 Hz, 2H), 3.68 (m, 1H), 2.89 (t, J = 5.7 Hz, 2H), 2.78 (t, J = 5.6 Hz, 2H), 2.74 (s, 3H), 2.33 (t, J = 5.6 Hz, 2H), 2.20 (s, 6H), 2.07-1.97 (m, 2H), 0.92-0.56 (m, 2H), 0.49-0.13 (m, 2H) |
| 23 | 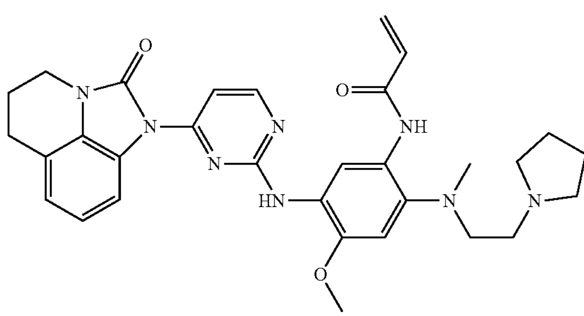 [SMILES: C=CC(=O)Nc1cc(Nc2nccc(-n3c(=O)n4c5c(cccc53)CCC4)n2)c(OC)cc1N(C)CCN1CCCC1] | N-(4-methoxy-2-(methyl(2-(pyrrolidin-1-yl)ethyl)amino)-5-((4-(2-oxo-5,6-dihydro-4H-imidazo[4,5,1-ij]quinolin-1(2H)-yl)pyrimidin-2-yl)amino)phenyl)acrylamide | MS (ESI): m/z = 569.4 [M + H]⁺, ¹H NMR (400 MHz, DMSO-d₆) δ 10.11 (s, 1H), 8.75 (s, 1H), 8.45-8.31 (m, 2H), 7.77 (m, 1H), 7.71 (d, J = 5.6 Hz, 1H), 7.04 (s, 1H), 6.92 (d, J = 7.6 Hz, 1H), 6.77 (t, J = 7.9 Hz, 1H), 6.38 (dd, J = 16.9, 10.1 Hz, 1H), 6.17 (dd, J = 16.9, 1.9 Hz, 1H), 5.71 (dd, J = 10.1, 1.9 Hz, 1H), 3.77 (t, J = 5.6 Hz, 2H), 3.73 (s, 3H), 2.90 (t, J = 5.7 Hz, 2H), 2.79 (t, J = 5.6 Hz, 2H), 2.75 (s, 3H), 2.32 (t, J = 5.6 Hz, 2H), 2.29-2.15 (m, 4H), 2.05-1.99 (m, 2H), 1.72-1.52 (m, 4H). |

Referring to the synthesis of compound 1, the compounds shown in the following table were obtained:

TABLE 3

| No | Structure | Name | MS |
|---|---|---|---|
| 24 | 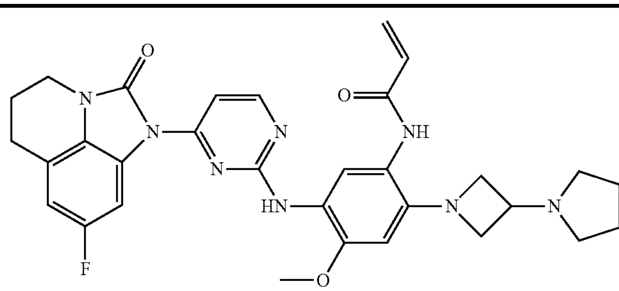 | N-(5-((4-(8-fluoro-2-oxo-5,6-dihydro-4H-imidazo[4,5,1-ij]quinolin-1(2H)-yl)pyrimidin-2-yl)amino)-4-methoxy-2-(3-(pyrrolidin-1-yl)azetidin-1-yl)phenyl)acrylamide | MS (ESI): m/z = 585.3 [M + H]⁺ |

TABLE 3-continued

| No | Structure | Name | MS |
|---|---|---|---|
| 25 | 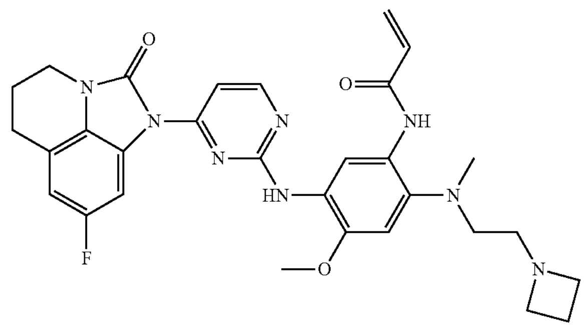 [SMILES: C=CC(=O)Nc1cc(Nc2nccc(-n3c(=O)n4c5c(cc(F)cc53)CCC4)n2)c(OC)cc1N(C)CCN1CCC1] | N-(2-((2-(azetidin-1-yl)ethyl)(methyl)amino)-5-((4-(8-fluoro-2-oxo-5,6-dihydro-4H-imidazo[4,5,1-ij]quinolin-1(2H)-yl)pyrimidin-2-yl)amino)-4-methoxyphenyl)acrylamide | MS (ESI): m/z = 573.3 [M + H]+ |
| 26 | 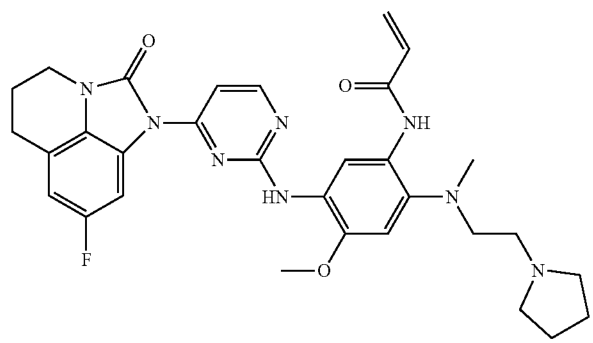 [SMILES: C=CC(=O)Nc1cc(Nc2nccc(-n3c(=O)n4c5c(cc(F)cc53)CCC4)n2)c(OC)cc1N(C)CCN1CCCC1] | N-(5-((4-(8-fluoro-2-oxo-5,6-dihydro-4H-imidazo[4,5,1-ij]quinolin-1(2H)-yl)pyrimidin-2-yl)amino)-4-methoxy-2-(methyl(2-(pyrrolidin-1-yl)ethyl)amino)phenyl)acrylamide | MS (ESI): m/z = 587.3 [M + H]+ |
| 27 | 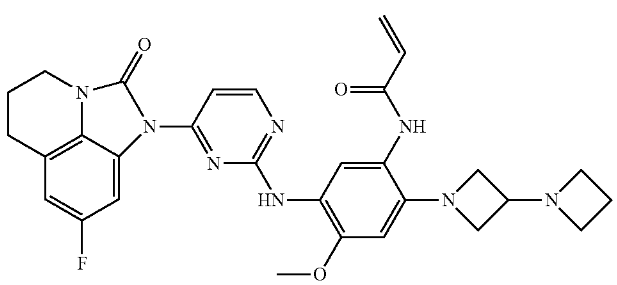 [SMILES: C=CC(=O)Nc1cc(Nc2nccc(-n3c(=O)n4c5c(cc(F)cc53)CCC4)n2)c(OC)cc1N1CC(N2CCC2)C1] | N-(2-([1,3'-biazetidin]-1'-yl)-5-((4-(8-fluoro-2-oxo-5,6-dihydro-4H-imidazo[4,5,1-ij]quinolin-1(2H)-yl)pyrimidin-2-yl)amino)-4-methoxyphenyl)acrylamide | MS (ESI): m/z = 571.3 [M + H]+ |
| 28 | 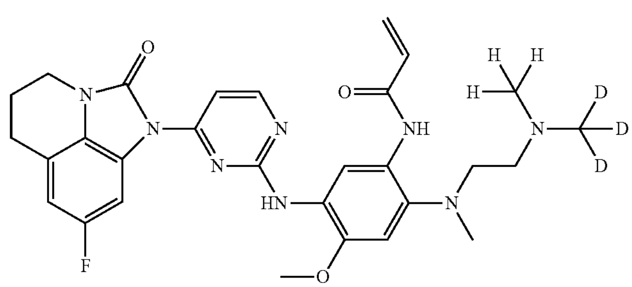 | N-(5-((4-(8-fluoro-2-oxo-5,6-dihydro-4H-imidazo[4,5,1-ij]quinolin-1(2H)-yl)pyrimidin-2-yl)amino)-4-methoxy-2-(methyl(2-(methyl(methyl-d3)amino)ethyl)amino)phenyl)acrylamide | MS (ESI): m/z = 564.3 [M + H]+ |
| 29 | 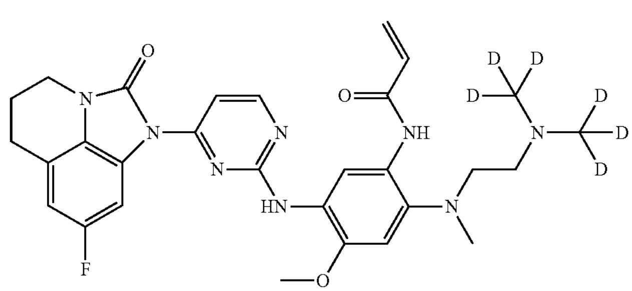 | N-(2-((2-(bis(methyl-d3)amino)ethyl)(methyl)amino)-5-((4-(8-fluoro-2-oxo-5,6-dihydro-4H-imidazo[4,5,1-ij]quinolin-1(2H)-yl)pyrimidin-2-yl)amino)-4-methoxyphenyl)acrylamide | MS (ESI): m/z = 567.3 [M + H]+ |

TABLE 3-continued

| No | Structure | Name | MS |
|----|-----------|------|----|
| 30 | 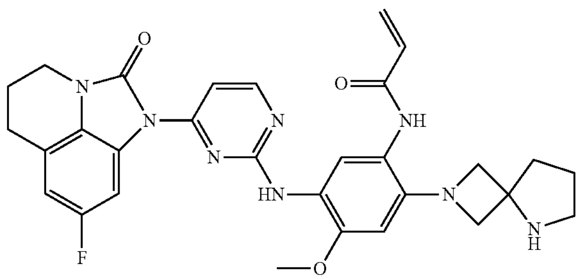 [SMILES: C=CC(=O)Nc1cc(Nc2nccc(-n3c(=O)n4c5c(cc(F)cc53)CCC4)n2)c(OC)cc1N1CC2(CCCN2)C1] | N-(5-((4-(8-fluoro-2-oxo-5,6-dihydro-4H-imidazo[4,5,1-ij]quinolin-1(2H)-yl)pyrimidin-2-yl)amino)-4-methoxy-2-(2,5-diazaspiro[3.4]octan-2-yl)phenyl)acrylamide | MS (ESI): m/z = 571.3 [M + H]+ |
| 31 | 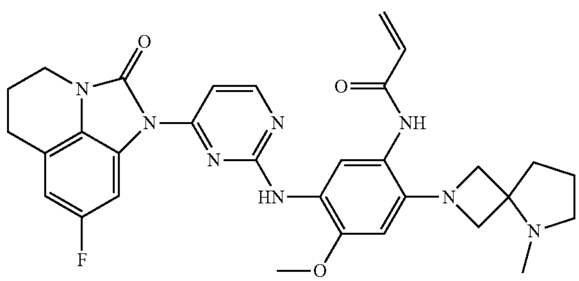 | N-(5-((4-(8-fluoro-2-oxo-5,6-dihydro-4H-imidazo[4,5,1-ij]quinolin-1(2H)-yl)pyrimidin-2-yl)amino)-4-methoxy-2-(5-methyl-2,5-diazaspiro[3.4]octan-2-yl)phenyl)acrylamide | MS (ESI): m/z = 585.3 [M + H]+ |
| 32 | 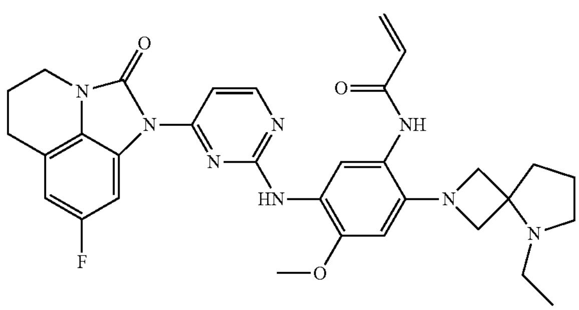 [SMILES: C=CC(=O)Nc1cc(Nc2nccc(-n3c(=O)n4c5c(cc(F)cc53)CCC4)n2)c(OC)cc1N1CC2(CCCN2CC)C1] | N-(2-(5-ethyl-2,5-diazaspiro[3.4]octan-2-yl)-5-((4-(8-fluoro-2-oxo-5,6-dihydro-4H-imidazo[4,5,1-ij]quinolin-1(2H)-yl)pyrimidin-2-yl)amino)-4-methoxyphenyl)acrylamide | MS (ESI): m/z = 599.3 [M + H]+ |
| 33 | 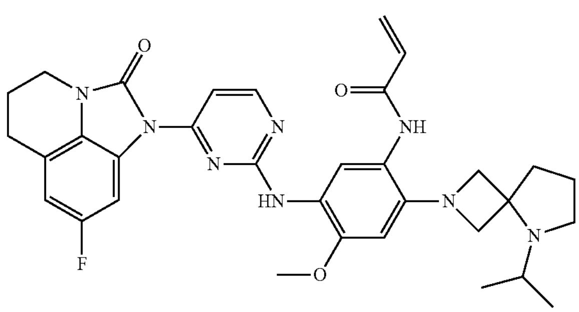 [SMILES: C=CC(=O)Nc1cc(Nc2nccc(-n3c(=O)n4c5c(cc(F)cc53)CCC4)n2)c(OC)cc1N1CC2(CCCN2C(C)C)C1] | N-(5-((4-(8-fluoro-2-oxo-5,6-dihydro-4H-imidazo[4,5,1-ij]quinolin-1(2H)-yl)pyrimidin-2-yl)amino)-2-(5-isopropyl-2,5-diazaspiro[3.4]octan-2-yl)-4-methoxyphenyl)acrylamide | MS (ESI): m/z = 613.3 [M + H]+ |
| 34 | 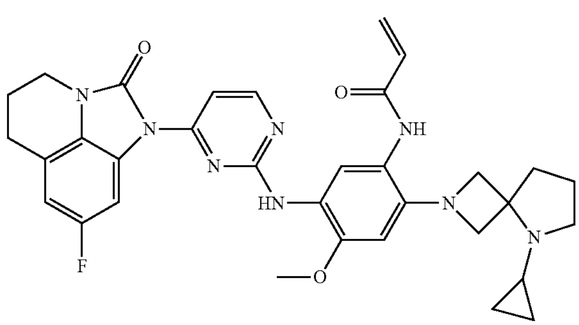 [SMILES: C=CC(=O)Nc1cc(Nc2nccc(-n3c(=O)n4c5c(cc(F)cc53)CCC4)n2)c(OC)cc1N1CC2(CCCN2C2CC2)C1] | N-(2-(5-cyclopropyl-2,5-diazaspiro[3.4]octan-2-yl)-5-((4-(8-fluoro-2-oxo-5,6-dihydro-4H-imidazo[4,5,1-ij]quinolin-1(2H)-yl)pyrimidin-2-yl)amino)-4-methoxyphenyl)acrylamide | MS (ESI): m/z = 611.3 [M + H]+ |

TABLE 3-continued

| No | Structure | Name | MS |
|---|---|---|---|
| 35 | 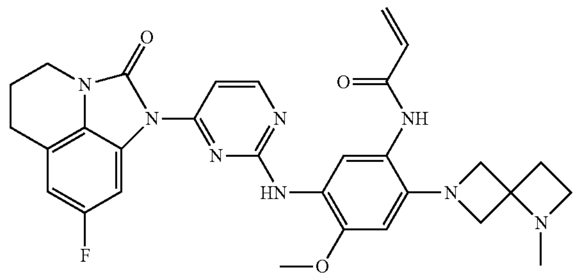 [SMILES: C=CC(=O)Nc1cc(Nc2nccc(-n3c(=O)n4c5c(cc(F)cc53)CCC4)n2)c(OC)cc1N1CC2(CCN2C)C1] | N-(5-((4-(8-fluoro-2-oxo-5,6-dihydro-4H-imidazo[4,5,1-ij]quinolin-1(2H)-yl)pyrimidin-2-yl)amino)-4-methoxy-2-(1-methyl-1,6-diazaspiro[3.3]heptan-6-yl)phenyl)acrylamide | MS (ESI): m/z = 571.3 [M + H]$^+$ |
| 36 | 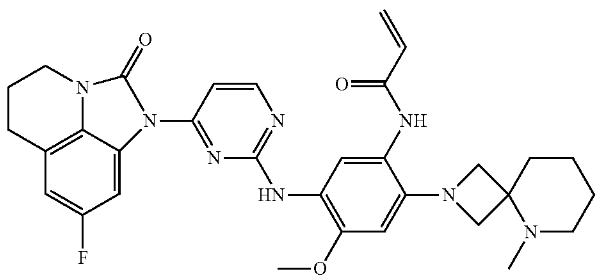 [SMILES: C=CC(=O)Nc1cc(Nc2nccc(-n3c(=O)n4c5c(cc(F)cc53)CCC4)n2)c(OC)cc1N1CC2(CCCCN2C)C1] | N-(5-((4-(8-fluoro-2-oxo-5,6-dihydro-4H-imidazo[4,5,1-ij]quinolin-1(2H)-yl)pyrimidin-2-yl)amino)-4-methoxy-2-(5-methyl-2,5-diazaspiro[3.5]nonan-2-yl)phenyl)acrylamide | MS (ESI): m/z = 599.3 [M + H]$^+$ |
| 37 | 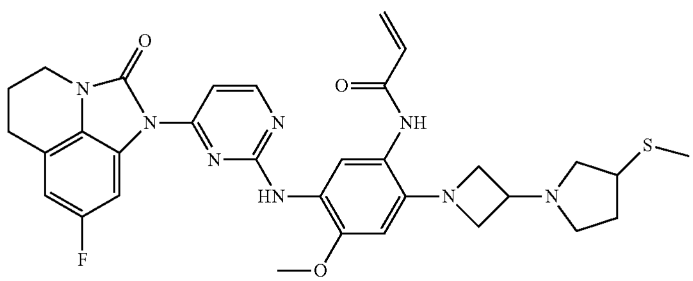 | N-(5-((4-(8-fluoro-2-oxo-5,6-dihydro-4H-imidazo[4,5,1-ij]quinolin-1(2H)-yl)pyrimidin-2-yl)amino)-4-methoxy-2-(3-(3-methoxypyrrolidin-1-yl)azetidin-1-yl)phenyl)acrylamide | MS (ESI): m/z = 615.3 [M + H]$^+$ |
| 38 | 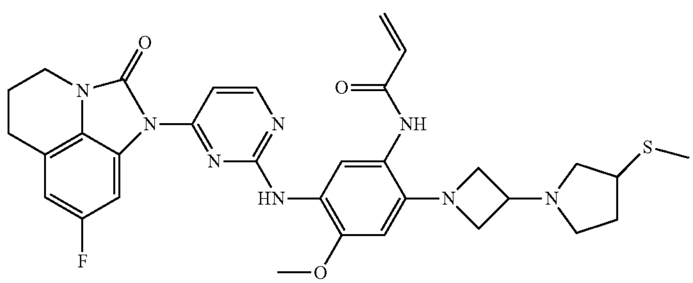 | N-(5-((4-(8-fluoro-2-oxo-5,6-dihydro-4H-imidazo[4,5,1-ij]quinolin-1(2H)-yl)pyrimidin-2-yl)amino)-4-methoxy-2-(3-(3-(methylthio)pyrrolidin-1-yl)azetidin-1-yl)phenyl)acrylamide | MS (ESI): m/z = 631.3 [M + H]$^+$ |
| 39 | 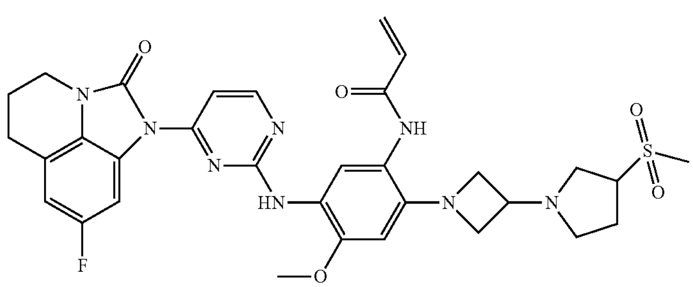 [SMILES: C=CC(=O)Nc1cc(Nc2nccc(-n3c(=O)n4c5c(cc(F)cc53)CCC4)n2)c(OC)cc1N1CC(N2CCC(S(C)(=O)=O)C2)C1] | N-(5-((4-(8-fluoro-2-oxo-5,6-dihydro-4H-imidazo[4,5,1-ij]quinolin-1(2H)-yl)pyrimidin-2-yl)amino)-4-methoxy-2-(3-(3-(methylsulfonyl)pyrrolidin-1-yl)azetidin-1-yl)phenyl)acrylamide | MS (ESI): m/z = 663.2 [M + H]$^+$ |

TABLE 3-continued

| No | Structure | Name | MS |
|----|-----------|------|----|
| 40 | 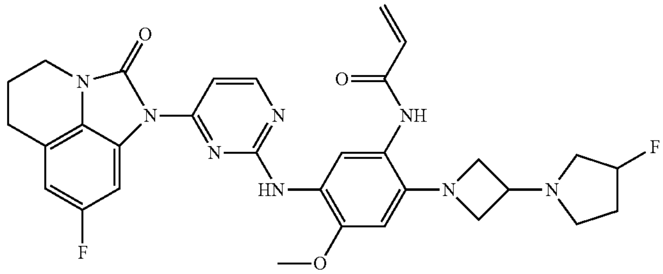 [SMILES: C=CC(=O)Nc1cc(Nc2nccc(-n3c(=O)n4c5c(cc(F)cc53)CCC4)n2)c(OC)cc1N1CC(N2CCC(F)C2)C1] | N-(5-((4-(8-fluoro-2-oxo-5,6-dihydro-4H-imidazo[4,5,1-ij]quinolin-1(2H)-yl)pyrimidin-2-yl)amino)-2-(3-(3-fluoropyrrolidin-1-yl)azetidin-1-yl)-4-methoxyphenyl)acrylamide | MS (ESI): m/z = 603.3 [M + H]+ |
| 41 | 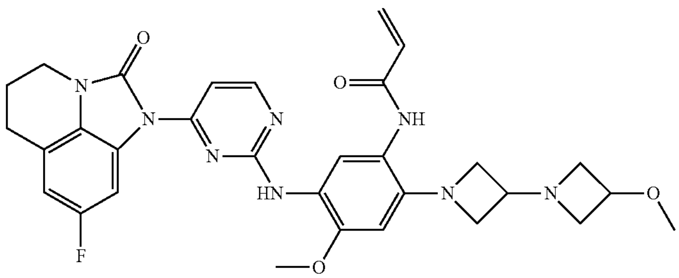 [SMILES: C=CC(=O)Nc1cc(Nc2nccc(-n3c(=O)n4c5c(cc(F)cc53)CCC4)n2)c(OC)cc1N1CC(N2CC(OC)C2)C1] | N-(5-((4-(8-fluoro-2-oxo-5,6-dihydro-4H-imidazo[4,5,1-ij]quinolin-1(2H)-yl)pyrimidin-2-yl)amino)-4-methoxy-2-(3-methoxy-[1,3'-biazetidin]-1'-yl)phenyl)acrylamide | MS (ESI): m/z = 601.3 [M + H]+ |
| 42 | 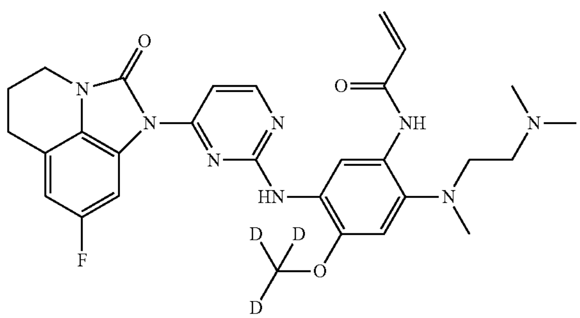 [SMILES: [2H]C([2H])([2H])Oc1cc(N(C)CCN(C)C)c(NC(=O)C=C)cc1Nc1nccc(-n2c(=O)n3c4c(cc(F)cc42)CCC3)n1] | N-(2-((2-(dimethylamino)ethyl)(methyl)amino)-5-((4-(8-fluoro-2-oxo-5,6-dihydro-4H-imidazo[4,5,1-ij]quinolin-1(2H)-yl)pyrimidin-2-yl)amino)-4-(methoxy-d3)phenyl)acrylamide | MS (ESI): m/z = 564.3 [M + H]+ |
| 43 | 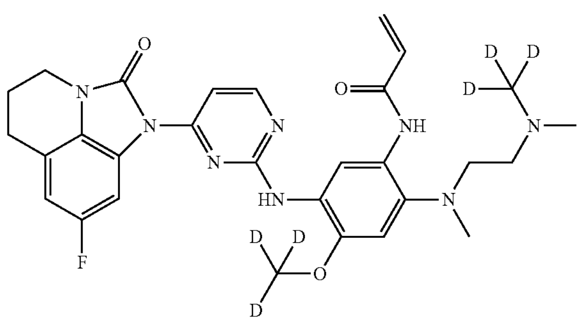 [SMILES: [2H]C([2H])([2H])Oc1cc(N(C)CCN(C)C([2H])([2H])[2H])c(NC(=O)C=C)cc1Nc1nccc(-n2c(=O)n3c4c(cc(F)cc42)CCC3)n1] | N-(5-((4-(8-fluoro-2-oxo-5,6-dihydro-4H-imidazo[4,5,1-ij]quinolin-1(2H)-yl)pyrimidin-2-yl)amino)-4-(methoxy-d3)-2-(methyl(2-(methyl(methyl-d3)amino)ethyl)amino)phenyl)acrylamide | MS (ESI): m/z = 567.3 [M + H]+ |
| 44 | 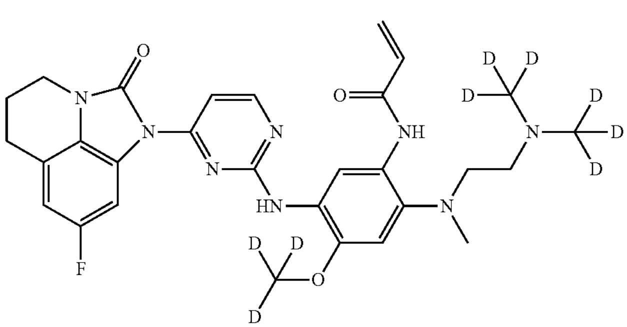 [SMILES: [2H]C([2H])([2H])Oc1cc(N(C)CCN(C([2H])([2H])[2H])C([2H])([2H])[2H])c(NC(=O)C=C)cc1Nc1nccc(-n2c(=O)n3c4c(cc(F)cc42)CCC3)n1] | N-(2-((2-(bis(methyl-d3)amino)ethyl)(methyl)amino)-5-((4-(8-fluoro-2-oxo-5,6-dihydro-4H-imidazo[4,5,1-ij]quinolin-1(2H)-yl)pyrimidin-2-yl)amino)-4-(methoxy-d3)phenyl)acrylamide | MS (ESI): m/z = 570.3 [M + H]+ |

Examples of Biological Assays of Compounds of the Present Invention

Assay 1: Wild-type EGFR, HER2 and HER4, and mutant EGFR biochemical activity assay 10 nL of Serially diluted compounds were transferred to assay plates using the labcyte Echo 550, and 5 uL of 2× enzymes in assay buffer were subsequently dispensed. The assay plate was covered with an adhesive plate seal, and briefly spinned for 30 s at 1000 g. 5 uL of 2× TK-substrate-biotin and ATP mixed in assay buffer were added.

After 40 minutes of incubation at room temperature, 10 uL of Sa-XL 665 and TK-antibody-Cryptate mixed in HTRF assay buffer were added to start the antibody binding.

After an additional of 60 min incubation at room temperature, the signals were measured with Envision 2104 at wavelengths of 615 nm (crypate) and 665 nm (XL665). The ratio of signals at 665 nm to 615 nm were calculated, and negative control values were used for normalization to calculate the percentage of inhibition. $IC_{50}$ was calculated and analyzed using a 4 parametric logistic model.

TABLE 4

|  | Compound 1 $IC_{50}$ (nM) | Compound 2 $IC_{50}$ (nM) | Compound 4 $IC_{50}$ (nM) | Compound 6 $IC_{50}$ (nM) | AZD9291 $IC_{50}$ (nM) |
|---|---|---|---|---|---|
| EGFR-WT | 1.559 | 1.232 | 0.5516 | 0.4512 | 2.903 |
| EGFR T790M/L858R | 0.0639 | 0.0724 | 0.0841 | 0.0865 | 0.1754 |
| EGFR Del19 | 0.1747 | 0.1069 | 0.2325 | 0.1399 | 1.160 |
| EGFR A763_Y764 insFHEA | 0.2642 | 0.2993 | 0.1426 | 0.1495 | 0.7831 |
| EGFR L792F | 1.256 | 1.649 | 0.415 | 4.095 | 10.14 |
| EGFR L792H | 27.64 | 46.89 | 15.56 | >100 | >100 |
| EGFR D770GY | 0.0649 | 0.2759 | 0.1298 | 0.0489 | 2.5760 |
| EGFR T790M | 0.0526 | 0.0509 | 0.0573 | 0.0656 | 0.1196 |
| EGFR D770_N771 insNPG T790M | 0.0490 | 0.0567 | 0.0514 | 0.0834 | 0.1339 |
| EGFR D770-N771insNPG | 0.0630 | 0.0815 | 0.0554 | 0.0688 | 0.4003 |
| HER2 | 35.11 | 47.01 | 34.64 | 25.11 | 83.19 |
| HER4 | 0.7693 | 1.3470 | 0.6935 | 0.7251 | 4.0080 |

As shown in the table above, compounds disclosed in this patent exhibits greater activity towards a broad spectrum of EGFR mutants including exon 20 insertions and point mutations than AZD9291. Superior activity was also observed with compounds not shown in the table.

Assay 2: A431 (wild type EGFR, skin cancer), H1975 (EGFR L858R/T790M, NSCLC) and Ba/F3 (EGFR D770_N771insSVD or EGFR V769_D770insASV, pro-B) cell proliferation assay A431 cells, H1975 and Ba/F3 cells expressing various mutant EGFR were harvested from exponential phase cultures and seeded in 96-well plates at a cell density of 3000 per well for A431 and H1975, and 10000 per well for Ba/F3 cells. After overnight attachment, compounds were 3-fold serially diluted and applied to cells at 30 μM, 10 μM, 3 μM, 1 μM, 0.3 μM, 0.1 M, 0.03 μM and 0.01 μM with triplicates, and incubated for three days. 20 μL of 5 mg/mL MTT was added afterwards followed by the further addition of 50 μL 10% SDS together with 5% isobutyl alcohol in 0.01 mol/L HCl. The plates were incubated overnight. Absorbance (A) at a wavelength of 570 nm was quantified. Percentage of inhibition was used for the calculation of $IC_{50}$ based on the bliss method. The results were shown in Table 5.

TABLE 5

|  | Ba/F3_EGFR D770_N771insSVD $IC_{50}$ (nM) | Ba/F3_EGFR V769_D770insASV $IC_{50}$ (nM) | H1975 $IC_{50}$ (nM) | A431 $IC_{50}$ (nM) |
|---|---|---|---|---|
| Compound 1 | 7.064 | 20.19 | 52.93 | 157.33 |
| Compound 2 | 9.146 | 23.8 | 22.99 | 71.09 |
| Compound 3 | 3.182 | 13.93 | 16.01 | 389.33 |
| Compound 4 | 5.077 | 15.68 | 12.43 | 153.50 |
| Compound 5 | 5.068 | 14.95 | 15.8 | 154.05 |
| Compound 6 | 3.469 | 13.33 | 14.85 | 139.72 |
| Compound 25 | 12.352 | 23.37 | 25.41 | 386.27 |
| Compound 28 | 5.133 | 14.35 | 32.18 | 256.32 |
| Compound 29 | 9.032 | 23.43 | 21.03 | 187.54 |
| Compound 42 | 5.609 | 13.86 | 14.63 | 301.22 |
| Compound 43 | 6.652 | 16.57 | 19.78 | 254.13 |
| AZD9291 | 61.11 | 179.2 | 14.61 | 419.37 |

In comparison with AZD9291, compounds in table 5 exhibit greater activity in inhibiting the proliferation of BaF$_3$ cells harboring EGFR D770_N771insSVD or EGFR V769_D770insAS, and comparable activity towards H1975 and A431, suggesting that compounds of the present disclosure demonstrate greatly improved activities towards EGFR exon 20 insertions, while maintaining potent activities towards EGFR L858R/T790M together with high selectivities over wild-type EGFR. Other examples of this application not listed in the table also showed similar activity profiles as described above.

Assay 3. In vivo studies in cell line-derived (CDX) and patient derived xenografts (PDX) mouse models Cells (H1975) or tissue pieces (LU0493 and LU0426) were implanted subcutaneously into the left armpit of nude mice. When the average tumor volume reached 100-150 mm$^3$, mice were randomized by tumor volume and treated with vehicle, compound 1 or poziotinib respectively. Tumor volume and body weight were measured twice per week. Mice were sacrificed on day 21 or day 28, and tumor volume and terminal body weight were recorded. The relative tumor volume, percent of treatment/control values and tumor growth inhibition were calculated and statistics was performed.

TABLE 6

| | TGI (%)/Terminal body weight changes (%) | | | |
|---|---|---|---|---|
| | LU-01-0493 | LU-01-0426 | LU-0387 | H1975 |
| Vehicle | NA/3.2 | NA/2.9 | NA/−9.43 | NA/8.5 |
| 15 mg/kg (compound 1) | 55.4/3.2 | 47/5.7 | NA/NA | 98/3.9 |
| 30 mg/kg (compound 1) | 72.3/−6.1 | 84/1.8 | 42/−7.75 | 106/5.1 |
| 60 mg/kg (compound 1) | 88.9/−6.5 | 106.3/−2 | 95/1.26 | 108/−4.1 |
| 0.5 mg/kg (poziotinib) | 56.8/−12.4 | 91.3/−7.4 | 74.49/0 | NA |

NA: none applicable

*: P<0.05 vs. vehicle group; D1: the first day of drug treatment; RTV: relative tumor volume; RTV=V$_t$/V$_0$; T/C (%)=T$_{RTV}$/C$_{RTV}$ X 100; T$_{RTV}$: RTV of the treatment group; C$_{RTV}$: RTV of the vehicle group; TGI (%): Tumor growth inhibition (%); T/C (%)>60: ineffective; T/C (%)≤60 and P<0.05: effective. Terminal body weight changes were calculated as percentage of body changes from day 1 to day 21.

As shown in the table above, compared to poziotinib, compound 1 is more effective in blocking tumor growth with EGFR exon 20 insertions and T790M mutations with less impacts on body weight, indicative of an increased safety margin.

Assay 4. In vivo orthotopic brain PC9 xenograft mouse model

3×10$^5$ PC9 cells expressing luciferase were injected to the mouse brain. Mice were randomized based on brain fluorescence intensity and body weight, and were orally administered vehicle or compound 1. Survival and body weights were monitored every day and mice with more than 20% body weight loss were sacrificed.

As shown in table 7 and FIG. 1, all mice in the vehicle group succumbed to death within 28 days after dosing, whereas, all mice receiving compound 1 survived, suggesting that compound 1 can enter the brain and inhibits tumor growth to promote survival.

TABLE 7

Effect of compound 1 on survival in orthotopic brain PC9 xenograft mouse model

| | Mice Survival Rate (%) | | | | | | |
|---|---|---|---|---|---|---|---|
| Compound | Day 16 | Day 17 | Day 18 | Day 22 | Day 24 | Day 26 | Day 28 |
| Vehicle | 87.5% | 75% | 50% | 37.5 | 12.5% | 0% | 0% |
| 30 mg/kg QD | 100% | 100% | 100% | 100% | 100% | 100% | 100% |
| 60 mg/kg QD | 100% | 100% | 100% | 100% | 100% | 100% | 100% |
| 60 mg/kg BID | 100% | 100% | 100% | 100% | 100% | 100% | 100% |

The results of Assays 1-4 show that the compound of this disclosure inhibits activity of mutant EGFR with exon 20 insertions and point mutations, and the proliferation of Ba/F3 cells harboring different EGFR mutations with a good selectivity over wild type EGFR. Compared to poziotinib, compound 1 showed greater in vivo efficacy in mouse PDX models with improved safety window. It is also active in PC9 orthotopic brain model indicative of a good brain penetration. Other compounds of the present disclosure are also efficacious in vivo in blocking tumor growth.

While specific embodiments of the invention have been described above, it will be understood by those skilled in the art that these are merely examples, and various changes or modifications may be made to these embodiments without departing from the principles and spirit of the invention. Accordingly, the scope of the invention is defined by the appended claims.

The invention claimed is:

1. A compound of general formula (I) or a pharmaceutically acceptable salt thereof:

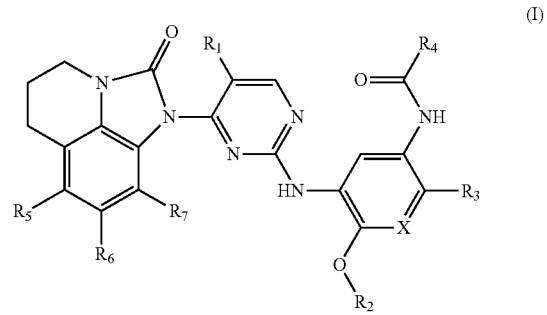

wherein:
X is selected from the group consisting of N and CH;
R$_1$ is selected from the group consisting of hydrogen, halogen, C1-6 alkyl, C3-6 cycloalkyl, —C(O)OR$_8$ and CN;
R$_2$ is selected from the group consisting of C1-6 alkyl, C3-6 cycloalkyl and C1-6 haloalkyl;
R$_3$ is selected from the group consisting of —NR$_9$(CH$_2$)$_2$NR$_9$'R$_9$" and

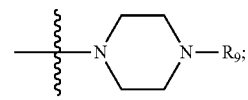

$R_4$ is

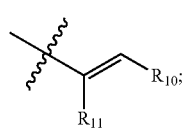

$R_5$, $R_6$, and $R_7$ are independently selected from the group consisting of hydrogen, halogen, C1-6 alkyl, C1-6 haloalkyl, C1-6 alkoxy and CN;
$R_8$ is selected from the group consisting of hydrogen, C1-6 alkyl and C1-6 haloalkyl;
$R_9$ is selected from the group consisting of hydrogen, C1-6 alkyl and C1-6 haloalkyl;
$R_9'$ and $R_9''$ are independently selected from the group consisting of hydrogen, C1-6 alkyl and C1-6 haloalkyl, or $R_9'$ and $R_9''$ together with the nitrogen connected thereto form a heterocycle, the heterocycle is unsubstituted or optionally substituted with 1-3 groups selected from the group consisting of halogen, C1-6 alkyl and C1-6 haloalkyl,
$R_{10}$ is selected from the group consisting of hydrogen, halogen, C1-6 alkyl and —$CH_2NR_{12}'R_{12}''$;
$R_{11}$ is selected from the group consisting of hydrogen, halogen and C1-6 alkyl; and
$R_{12}$ and $R_{12}'$ are independently selected from the group consisting of hydrogen, C1-6 alkyl and C1-6 haloalkyl, or $R_{12}'$ and $R_{12}''$ together with the nitrogen connected thereto form a heterocycle, the heterocycle is unsubstituted or optionally substituted with 1-3 groups selected from the group consisting of halogen, C1-6 alkyl and C1-6 haloalkyl.

2. The compound of general formula (I) or a pharmaceutically acceptable salt thereof according to claim 1, wherein:
$R_1$ is selected from the group consisting of hydrogen, halogen, C1-6 alkyl, —$C(O)OR_8$ and CN; and
$R_5$, $R_6$ and $R_7$ are independently selected from the group consisting of hydrogen and halogen.

3. The compound of general formula (I) or a pharmaceutically acceptable salt thereof according to claim 2, wherein the compound is:

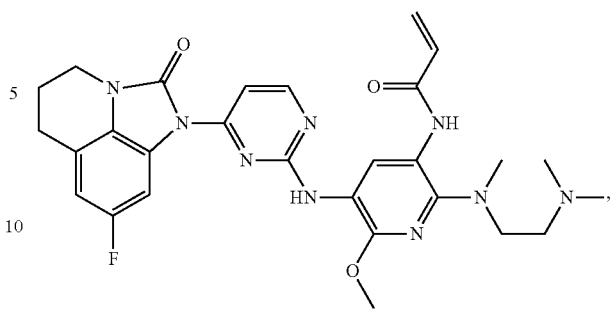

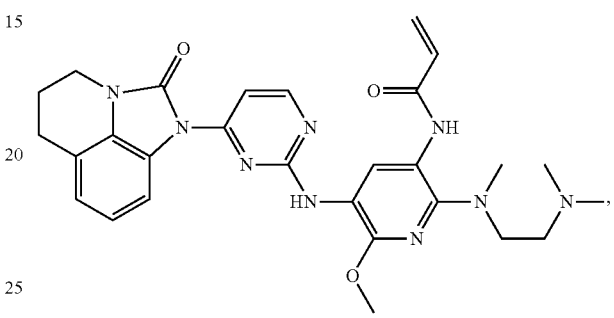

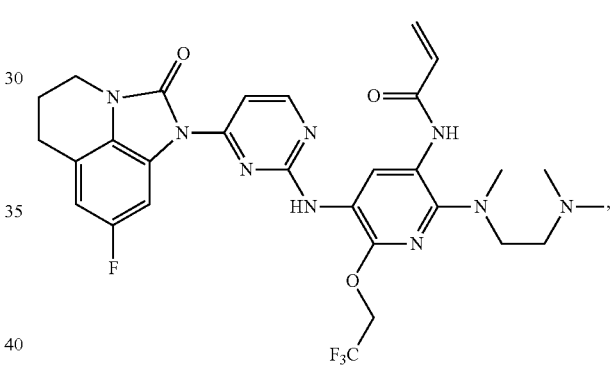

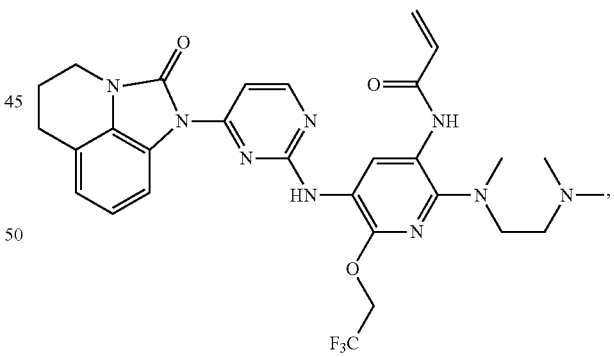

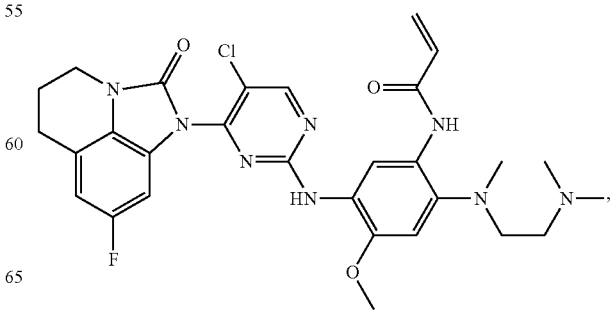

69
-continued
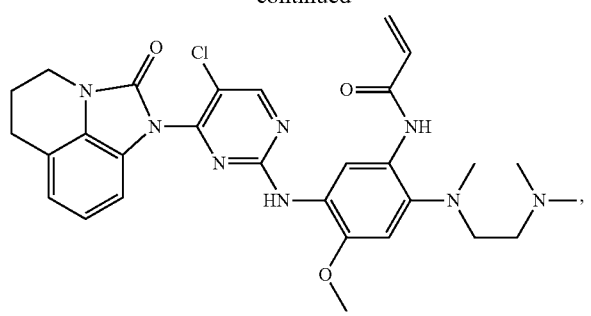
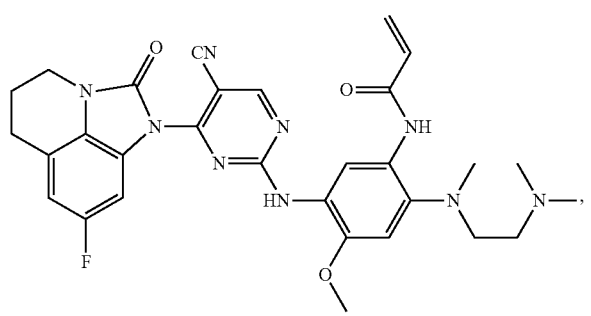
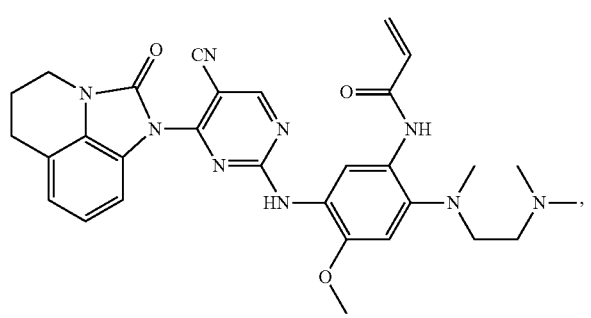
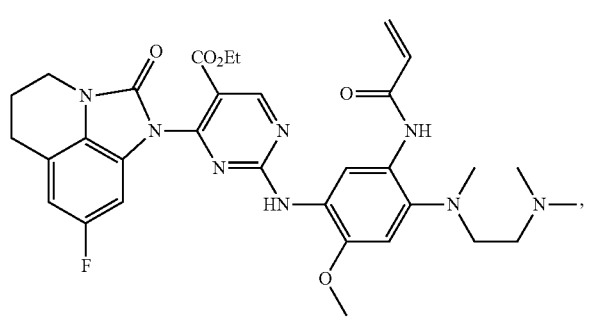
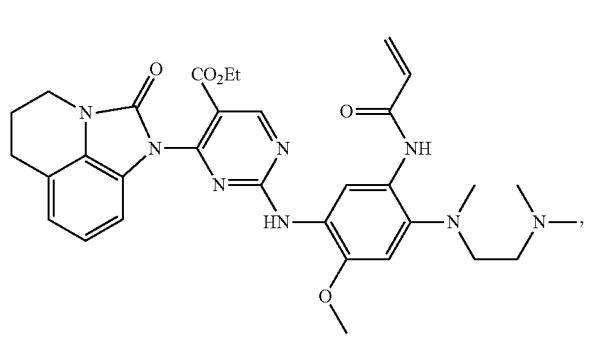
70
-continued
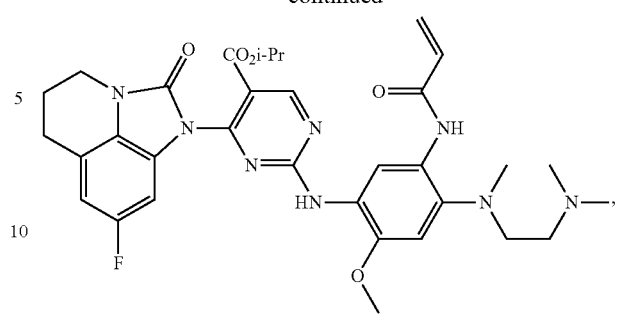
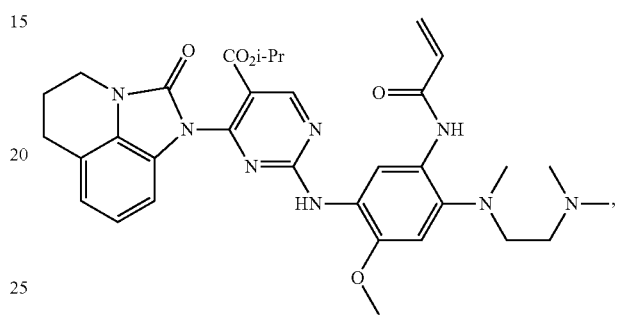
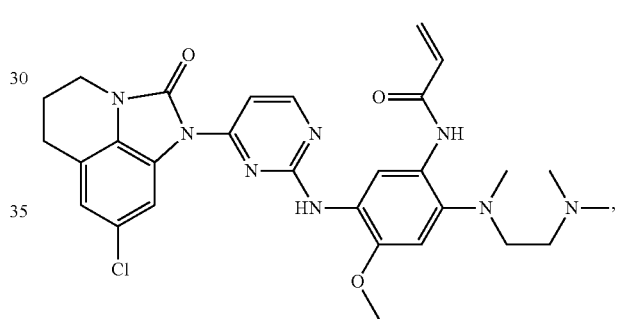
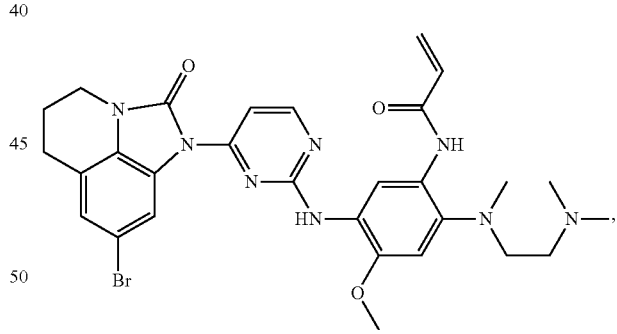
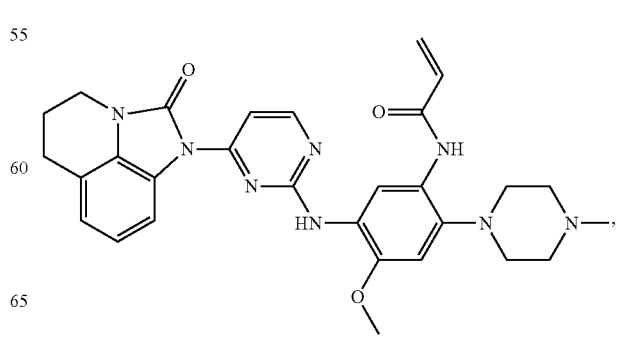

71
-continued
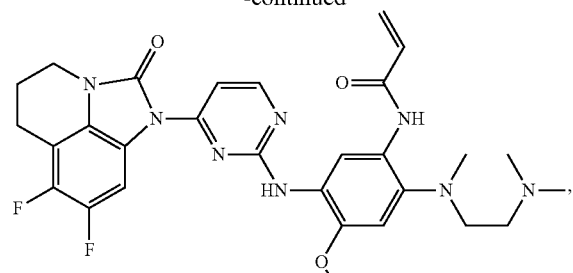
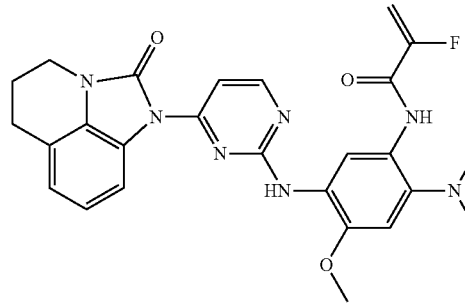
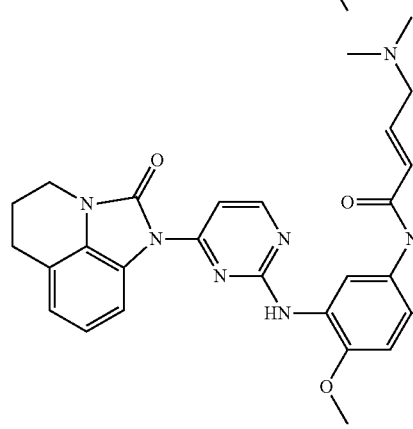
72
-continued
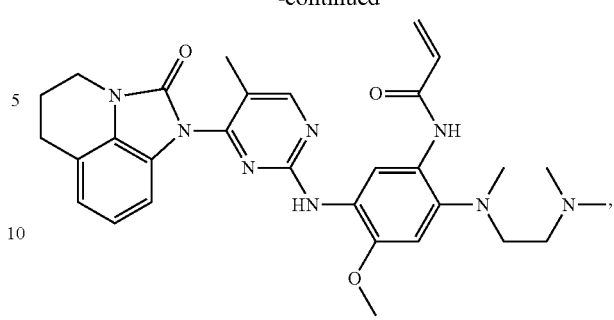
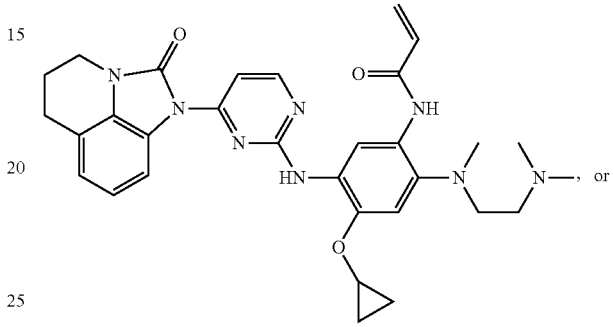
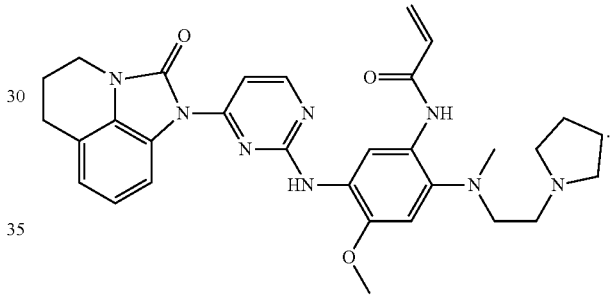
* * * * *